(12) United States Patent
Hemberger et al.

(10) Patent No.: US 8,916,518 B2
(45) Date of Patent: *Dec. 23, 2014

(54) COUPLING PROTEINS TO A MODIFIED POLYSACCHARIDE

(75) Inventors: Jurgen Hemberger, Aschaffenburg (DE); Michele Orlando, The Hague (NL); Klaus Sommermeyer, Rosbach v.d.H (DE); Wolfram Eichner, Butzbach (DE); Sven Frie, Bramois (CH); Katharina Lutterbeck, Friedberg (DE); Cornelius Jungheinrich, Bad Homburg (DE); Roland Scharpf, Ranstadt (DE)

(73) Assignee: Fresenius Kabi Deutschland GmbH, Bad Homburg v.d.H. (DE)

( * ) Notice: Subject to any disclaimer, the term of this patent is extended or adjusted under 35 U.S.C. 154(b) by 686 days.

This patent is subject to a terminal disclaimer.

(21) Appl. No.: 12/473,462

(22) Filed: May 28, 2009

(65) Prior Publication Data

US 2009/0233847 A1 Sep. 17, 2009

Related U.S. Application Data

(63) Continuation of application No. 10/506,367, filed as application No. PCT/EP03/02083 on Feb. 28, 2003, now Pat. No. 7,541,328.

(30) Foreign Application Priority Data

Mar. 6, 2002 (DE) .................. 102 09 821

(51) Int. Cl.
| | | |
|---|---|---|
| A61K 38/00 | (2006.01) | |
| C07K 14/00 | (2006.01) | |
| C08B 31/00 | (2006.01) | |
| A61K 47/48 | (2006.01) | |
| C08H 1/00 | (2006.01) | |
| C08B 31/18 | (2006.01) | |

(52) U.S. Cl.
CPC ............... *C08B 31/185* (2013.01); *C08B 31/00* (2013.01); *A61K 47/4823* (2013.01); *C08H 1/00* (2013.01); *C08B 31/18* (2013.01)
USPC ............................... 514/2; 530/300; 530/350

(58) Field of Classification Search
None
See application file for complete search history.

(56) References Cited

U.S. PATENT DOCUMENTS

| | | | |
|---|---|---|---|
| 3,191,291 A | 6/1965 | Maier | |
| 3,226,395 A | 12/1965 | Schimmelschmidt et al. | |
| 4,001,200 A | 1/1977 | Bonsen et al. | |
| 4,001,401 A | 1/1977 | Bonsen et al. | |
| 4,053,590 A | 10/1977 | Bonsen et al. | |
| 4,061,736 A | 12/1977 | Morris et al. | |
| 4,064,118 A | 12/1977 | Wong | |
| 4,125,492 A | 11/1978 | Cuatrecasas et al. | |
| 4,179,337 A | 12/1979 | Davis et al. | |
| 4,261,973 A | 4/1981 | Lee et al. | |
| 4,412,989 A | 11/1983 | Iwashita et al. | |
| 4,454,161 A | 6/1984 | Okada et al. | |
| 4,496,689 A | 1/1985 | Mitra | |
| 4,667,016 A | 5/1987 | Lai et al. | |
| 4,703,008 A | 10/1987 | Lin | |
| 4,766,106 A | 8/1988 | Katre et al. | |
| 4,847,325 A | 7/1989 | Shadle et al. | |
| 4,863,964 A | 9/1989 | Hedlund et al. | |
| 4,900,780 A | 2/1990 | Cerny | |
| 4,904,584 A | 2/1990 | Shaw | |
| 4,925,677 A | 5/1990 | Feijen | |
| 4,939,239 A | 7/1990 | Matsuhashi et al. | |
| 4,952,496 A | 8/1990 | Studier et al. | |
| 5,068,321 A | 11/1991 | Buysch et al. | |
| 5,073,628 A | 12/1991 | Matsuhashi et al. | |
| 5,079,337 A | 1/1992 | Leonard | |
| 5,110,909 A | 5/1992 | Dellacherie et al. | |
| 5,214,132 A | 5/1993 | Kuga et al. | |
| 5,217,998 A | 6/1993 | Hedlund et al. | |
| 5,218,092 A | 6/1993 | Sasaki et al. | |
| 5,218,108 A | 6/1993 | Sommermeyer et al. | |

(Continued)

FOREIGN PATENT DOCUMENTS

| | | |
|---|---|---|
| AU | 5238393 | 9/1993 |
| CA | 2 110 543 | 6/1994 |
| CA | 2 233 725 | 9/1999 |
| CA | 2 441 442 | 9/2003 |
| CA | 2 478 478 | 1/2004 |
| CA | 2 478 480 | 1/2004 |
| DE | 22 33 977 | 2/1973 |
| DE | 26 16 086 | 11/1977 |
| DE | 30 29 307 | 3/1982 |
| DE | 35 01 616 | 7/1986 |

(Continued)

OTHER PUBLICATIONS

Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.

(Continued)

*Primary Examiner* — Anand Desai
(74) *Attorney, Agent, or Firm* — Fish & Richardson P.C.

(57) ABSTRACT

The invention relates to a method for coupling proteins to a starch-derived modified polysaccharide. The binding interaction between the modified polysaccharide and the protein is based on a covalent bond which is the result of a coupling reaction between the terminal aldehyde group or a functional group of the modified polysaccharide molecule resulting from the chemical reaction of this aldehyde group and a functional group of the protein which reacts with the aldehyde group or with the resulting functional group of the polysaccharide molecule. The bond directly resulting from the coupling reaction can be optionally modified by a further reaction to the aforementioned covalent bond. The invention further relates to pharmaceutical compositions that comprise conjugates formed in this coupling process and to the use of conjugates and compositions for the prophylaxis or therapy of the human or animal body.

25 Claims, No Drawings

(56) References Cited

U.S. PATENT DOCUMENTS

| | | | |
|---|---|---|---|
| 5,281,698 A | 1/1994 | Nitecki | |
| 5,342,770 A | 8/1994 | Yamasaki | |
| 5,362,853 A | 11/1994 | Kuga et al. | |
| 5,420,105 A | 5/1995 | Gustavson et al. | |
| 5,470,843 A | 11/1995 | Stahl et al. | |
| 5,484,903 A | 1/1996 | Szablikowski et al. | |
| 5,543,332 A | 8/1996 | Lihme et al. | |
| 5,581,476 A | 12/1996 | Osslund | |
| 5,622,718 A | 4/1997 | Al-Shamkhani et al. | |
| 5,723,589 A | 3/1998 | Miljkovic et al. | |
| 5,736,533 A | 4/1998 | Simon et al. | |
| 5,770,645 A | 6/1998 | Stamler | |
| 5,824,778 A | 10/1998 | Ishikawa et al. | |
| 5,840,900 A | 11/1998 | Greenwald | |
| 5,847,110 A | 12/1998 | Dragsten et al. | |
| 5,851,984 A | 12/1998 | Matthews et al. | |
| 5,876,980 A | 3/1999 | DeFrees et al. | |
| 5,880,270 A | 3/1999 | Berninger et al. | |
| 5,952,347 A | 9/1999 | Arison et al. | |
| 5,977,163 A | 11/1999 | Li et al. | |
| 5,981,507 A | 11/1999 | Josephson et al. | |
| 5,990,237 A | 11/1999 | Bentley et al. | |
| 6,011,008 A | 1/2000 | Domb et al. | |
| 6,083,909 A | 7/2000 | Sommermeyer et al. | |
| 6,172,208 B1 | 1/2001 | Cook | |
| 6,261,800 B1 | 7/2001 | Nikolics et al. | |
| 6,299,881 B1 | 10/2001 | Lees et al. | |
| 6,340,746 B1 | 1/2002 | Roberts et al. | |
| 6,375,846 B1 | 4/2002 | Jarrett et al. | |
| 6,395,266 B1 | 5/2002 | Martinez et al. | |
| 6,417,347 B1 | 7/2002 | Herrmann | |
| 6,451,337 B1 | 9/2002 | Smith et al. | |
| 6,500,930 B2 | 12/2002 | Adamson | |
| 6,544,503 B1 | 4/2003 | Vanderhoff | |
| 6,555,660 B2 | 4/2003 | Nissen et al. | |
| 6,586,398 B1 | 7/2003 | Kinstler et al. | |
| 6,596,135 B1 | 7/2003 | Mitsui | |
| 6,596,861 B1 | 7/2003 | Moreau | |
| 6,624,142 B2 | 9/2003 | Greenwald | |
| 6,660,843 B1 | 12/2003 | Feige et al. | |
| 6,875,594 B2 | 4/2005 | Muir et al. | |
| 6,916,962 B2 | 7/2005 | Rosen et al. | |
| 7,115,576 B2 | 10/2006 | Sommermeyer | |
| 7,125,843 B2 | 10/2006 | DeFrees et al. | |
| 7,157,546 B2 | 1/2007 | Kozlowski | |
| 7,179,617 B2 | 2/2007 | DeFrees et al. | |
| 7,279,176 B1 | 10/2007 | West | |
| 7,285,661 B2 | 10/2007 | Sommermeyer et al. | |
| 7,538,092 B2 | 5/2009 | Orlando et al. | |
| 7,541,328 B2 | 6/2009 | Hemberger | |
| 7,629,456 B2 | 12/2009 | Lange et al. | |
| 7,815,893 B2 | 10/2010 | Zander et al. | |
| 7,816,516 B2 | 10/2010 | Sommermeyer et al. | |
| 8,017,739 B2 | 9/2011 | Eichner et al. | |
| 2002/0065410 A1 | 5/2002 | Antrim | |
| 2002/0151006 A1 | 10/2002 | Muir et al. | |
| 2003/0087877 A1 | 5/2003 | Calias et al. | |
| 2003/0191291 A1 | 10/2003 | Kochendoerfer et al. | |
| 2004/0023306 A1 | 2/2004 | Aebersold et al. | |
| 2004/0043446 A1 | 3/2004 | DeFrees et al. | |
| 2004/0180858 A1 | 9/2004 | Sommermeyer | |
| 2005/0063943 A1 | 3/2005 | Sommermeyer et al. | |
| 2005/0181985 A1 | 8/2005 | Hemberger et al. | |
| 2005/0238723 A1 | 10/2005 | Zander et al. | |
| 2006/0019877 A1 | 1/2006 | Conradt et al. | |
| 2006/0121062 A1 | 6/2006 | Eichner et al. | |
| 2006/0188472 A1 | 8/2006 | Sommermeyer et al. | |
| 2006/0194940 A1 | 8/2006 | Kozlowski | |
| 2006/0217293 A1 | 9/2006 | Orlando et al. | |
| 2007/0087961 A1 | 4/2007 | Eichner et al. | |
| 2007/0134197 A1 | 6/2007 | Eichner et al. | |
| 2008/0206182 A1 | 8/2008 | Sommermeyer et al. | |
| 2008/0207562 A1 | 8/2008 | Zander et al. | |
| 2008/0274948 A1* | 11/2008 | Eichner et al. | 514/8 |
| 2009/0091549 A1 | 4/2009 | Matsumoto et al. | |
| 2009/0233847 A1 | 9/2009 | Hemberger et al. | |
| 2010/0062973 A1* | 3/2010 | Frank et al. | 514/8 |
| 2010/0297078 A1* | 11/2010 | Hacket et al. | 424/85.7 |
| 2010/0305033 A1* | 12/2010 | Hacket et al. | 514/7.7 |
| 2010/0311670 A1* | 12/2010 | Zander et al. | 514/20.9 |
| 2010/0317609 A1* | 12/2010 | Zander et al. | 514/43 |
| 2011/0054152 A1 | 3/2011 | Zander et al. | |
| 2011/0200555 A1* | 8/2011 | Eichner et al. | 424/85.6 |

FOREIGN PATENT DOCUMENTS

| | | |
|---|---|---|
| DE | 26 46 854 | 5/1989 |
| DE | 38 36 600 | 5/1990 |
| DE | 279 486 | 6/1990 |
| DE | 41 30 807 | 3/1993 |
| DE | 26 07 706 | 5/1993 |
| DE | 69025920 | 8/1996 |
| DE | 196 28 705 | 1/1998 |
| DE | 198 08 079 | 8/1999 |
| DE | 100 41 541 | 3/2002 |
| DE | 101 12 825 | 10/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 218 825 | 4/1987 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 338 916 | 10/1989 |
| EP | 0 402 724 | 6/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0 640 619 | 3/1995 |
| EP | 0 646 130 | 4/1995 |
| EP | 0 418 523 | 6/1995 |
| EP | 0 661 294 | 7/1995 |
| EP | 0 668 351 | 8/1995 |
| EP | 0 809 996 | 5/1996 |
| EP | 0 806 140 | 11/1997 |
| EP | 1 064 951 | 1/2001 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| EP | 1 496 076 | 1/2005 |
| EP | 1 591 467 | 11/2005 |
| EP | 2 070 950 | 6/2009 |
| EP | 2 143 736 | 1/2010 |
| EP | 2 154 160 | 2/2010 |
| EP | 1 660 134 | 12/2010 |
| EP | 1372735 | 10/2011 |
| FR | 2 378 094 | 8/1978 |
| GB | 1 419 080 | 12/1975 |
| GB | 1 549 246 | 10/1976 |
| GB | 1 540 428 | 2/1979 |
| IL | 166506 | 2/2010 |
| JP | 10-287554 | 10/1998 |
| JP | 2001-294601 | 10/2001 |
| WO | WO 80/02374 | 11/1980 |
| WO | WO 90/07939 | 7/1990 |
| WO | WO 90/12874 | 11/1990 |

(56) References Cited

FOREIGN PATENT DOCUMENTS

| WO | WO 90/15628 | 12/1990 |
|---|---|---|
| WO | WO 92/11037 | 7/1992 |
| WO | WO 93/23062 | 11/1993 |
| WO | WO 93/24476 | 12/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | WO 98/01158 | 1/1998 |
| WO | WO 98/05689 | 2/1998 |
| WO | WO 98/07713 | 2/1998 |
| WO | WO 98/08856 | 3/1998 |
| WO | WO 98/14212 | 4/1998 |
| WO | WO 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | WO 99/17783 | 4/1999 |
| WO | WO 99/49897 | 10/1999 |
| WO | WO 00/07738 | 2/2000 |
| WO | WO 00/18893 | 4/2000 |
| WO | WO 00/55210 | 9/2000 |
| WO | WO 00/66633 | 9/2000 |
| WO | WO 00/78355 | 12/2000 |
| WO | WO 01/70272 | 9/2001 |
| WO | WO 01/78682 | 10/2001 |
| WO | WO 01/83522 | 11/2001 |
| WO | WO 01/85799 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/080979 | 10/2002 |
| WO | WO 03/000738 | 1/2003 |
| WO | WO 03/031464 | 4/2003 |
| WO | WO 03/031581 | 4/2003 |
| WO | WO 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | WO 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | WO 2005/072778 | 8/2005 |
| WO | WO 2005/074993 | 8/2005 |
| WO | WO 2005/083103 | 9/2005 |
| WO | WO 2005/092369 | 10/2005 |
| WO | WO 2005/092390 | 10/2005 |
| WO | WO 2005/112954 | 12/2005 |
| WO | WO 2006/108052 | 10/2006 |
| WO | WO 2007/053292 | 5/2007 |
| WO | WO2010/042638 | 4/2010 |

OTHER PUBLICATIONS

Adamczyk and Fishpaugh, "A Solid Supported Synthesis of Thiol Esters," *Tetrahedron Lett.*, 1996, 37(25):4305-4308.

Alagon et al., "Activation of Polysaccharides with 2-1minothiolane and its uses," *Biochem.* 1980, 19:4341-4345.

Alayash and Cashon, "Hemoglobin and free radicals: implications for the development of a safe blood substitute," *Mol. Med. Today*, 1995, 1(3):122-127.

Aly et al., "Hemophilia A due to mutations that create new N-glycosylation sites," *Proc. Natl. Acad. Sci. USA*, 1992, 89:4933-4937.

Anderson and Meister, "Inhibition of y-glutamyl transpeptidase and induction of glutathionuria by y-glutamyl amino acids," *Proc. Natl. Acad. Sci. USA*, 1986, 83:5029-5032.

Andersson et al., "Isolation and characterization of human factor VIII: Molecular forms in commercial factor VIII concentrate, cryoprecipitate, and plasma," *Proc. Natl. Acad. Sci. USA*, 1986, 83:2979-2983.

Anno et al., "Basics of Sugar chemistry," 1995, pp. 1-5, (w/ translation).

Armitage, "Emerging Applications of Recombinant Human Granulocyte-Macrophage Colony-Stimulating Factor," *Blood*, 1998, 92(12):4491-4508.

Ashwell, "Carbohydrate Antigens: Coupling of Carbohydrates to Proteins by a Mixed Anhydride Reaction," *Meth. Enzymol.*, 1972, 28:219-222.

Avigad, "A Simple Spectrophotometric Determination of Formaldehyde and Other Aldehydes: Application to Periodate-Oxidized Glycol Systems," *Anal. Biochem.*, 1983, 134:499-504.

Axèn et al., "Chemical Coupling of Peptides and Proteins to Polysaccharides by Means of Cyanogen Halides," *Nature*, 1967, 214:1302-1304.

Balazy et al., "S-Nitroglutathione, a Product of the Reaction between Peroxynitrite and Glutathione that Generates Nitric Oxide," *J. Biol. Chem.*, 1998, 273(48): 32009-32015.

Baldwin et al., "Synthesis of Polymer-Bound Hemoglobin Samples," *Tetrahedron*, 1981, 37:1723-1726.

Balland et al., "Characterisation of two differently processed forms of human recombinant factor IX synthesised in CHO cells transformed with a polycistronic vector," *Eur. J. Biochem.*, 1988, 172(3):565-572.

Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.

Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.

Bauer and Rosenberg, "Role of Antithrombin III as a Regulator of In Vivo Coagulation," *Semin. Hematol.*, 1991, 28:10-18.

Bauer and Suresh, "S-[w-(Aminoöxy)alkyl]isothiuronium Salts, w,w'-Bis(aminoöxy)alkanes and Related Compounds," *J. Org. Chem.*, 1963, 28:1604-1608.

Bauer et al., "Synthesis of w—(Aminooxy)alkanethiols," *J. Org. Chem.*, 1965, 30:949-951.

Bayer et al., The Avidin-Biotin Complex in Affinity Cytochemistry, *Meth. Enzymol.*, 1979, 62:308-315.

Bendele et al., "Short Communication: Renal Tubular Vacuolation in Animals Treated with Polyethylene-Glycol-Conjugated Proteins," *Toxicol. Sci.*, 1998, 42:152-157.

Benesch, "Bis(pyridoxal) Polyphosphates as Specific Intramolecular Cross-Linking Agents for Hemoglobin," *Meth. Enzymol.*, 1994, 231:267-274.

(56) References Cited

OTHER PUBLICATIONS

Bepperling et al., "HES 130/0.4, a new HES specification: tissue storage after multiple infusions in rats," *Crit. Care*, 1999, 3(suppl 1):p. 153.

Berg et al., "Engineering the proteolytic specificity of activated protein C improves its pharmacological properties," *Proc. Natl. Acad. Sci. USA*, 2003, 100(8):4423-4428.

Berger et al., "Galactosyltransferase-dependent sialylation of complex and endo-N-acetylglucosaminidase H-treated core N-glycans in vitro," *FEBS Lett.*, 1986, 203(1):64-68.

Bernardes et al. "The Direct Formation of GlycosylThiols from Reducing Sugars Allows One-Pot Protein Glycoconjugation," *Angew Chem.* 2006, 118: 4111-4115.

Besheer et al., "Enzymatically Catalyzed HES Conjugation Using Microbial Transglutaminase: Proof of Feasibility," *J. Pharm. Sci.* 98 (11): 4420-4428 (2009).

Bhattacharyya et al., "Recombinant Factor VIII for Haemophilia An Overview of Production Technologies," *CRIPS*, 2003, 4(3):2-8.

Björk and Danielsson, "Antithrombin and related inhibitors of coagulation proteinases," *Proteinase Inhibitors*, 1986, Chapter 17, pp. 489-513.

Black et al., "N-Bromoacetyl-glycopyranosylamines as affinity labels for a β-glucosidase and a cellulase," *Carbohydr. Res.*, 1993, 250:195-202.

Blum et al., "Improved silver staining of plant proteins, RNA and DNA in polyacrylamide gels," *Electrophoresis*, 1987, 8:93-99.

Bobbitt, "Periodate Oxidation of Carbohydrates," *Carbohydr. Chem.*, 1956, 11:1-41.

Boissel et al., "Erythropoietin Structure-Function Relationships. Mutant proteins that test a model of tertiary structure," *J. Biol. Chem.*, 1993, 268(21):15983-15993.

Boorsma et al., "Bioprocess Applications of a Sindbis Virus-Based Temperature-Inducible Expression System," *Biotech. Bioeng.*, 2002, 79(6): 602-609.

Boturyn et al., "Synthesis of Fluorescent Probes for the Detection of Abasic Sites in DNA," *Tetrahedron*, 1997, 53(15):5485-5492.

Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.

Boyer et al., "Reaction in Biphasic Water/Organic Solvent System in the Presence of Surfactant: Inverse Phase Transfer Catalysis versus Interfacial Catalysis," *Tetrahedron*, 2000, 56:303-307.

Bronzino, *The Biomedical Engineering Handbook*, CRC Press, USA, Salem, 1995, (TOC only).

Bunn and Jandl, "The Renal Handling of Hemoglobin. II. Catabolism," *J. Exp. Med.*, 1967, 129:925-934.

Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation," *Glycoconj. J.*, 1999, 16:691-695.

Cabacungan et al., "Amine Boranes as Alternative Reducing Agents for Reductive Alkylation of Proteins," *Anal. Biochem.*, 1982, 124:272-278.

Caliceti et al., "Immunological Properties of Uriease Conjugated to Neutral Soluble Polymers," *Bioconjugate Chem.*, 2001, 12:515-522.

Carey and Sundberg, *Organische Chemie*, VCH *Verlagsgesellschaft mbH*, Weinheim (DE), 1995.

Carlsson et al., "Protein Thiolation and Reversible Protein-Protein Conjugation," *Biochem J.*, 1978, 173:723-737.

Carrell et al., "Human $\alpha_1$-antitrypsin: carbohydrate attachment and sequence homology," *FEBS Lett.*, 1981, 135(2):301-303.

Carrell et al., "Structural Mobility of Antithrombin and its Modulation by Heparin," *Thromb. Haemost.*, 1997, 78:516-519.

Carver et al., "Expression of human α1 antitrypsin in transgenic sheep," *Cytotechnology*, 1992, 9:77-84.

Castillo et al., "Sensitive Substrates for Human Leukocyte and Porcine Pancreatic Elastase: A Study of the Merits of Various Chromophoric and Fluorogenic Leaving Groups in Assays for Serine Proteases," *Anal. Biochem.*, 1979, 99:53-64.

Cavallaro et al., "Folate-mediated targeting of polymeric conjugates of gemcitabine," *Int. J. Pharmaceut.*, 2006, 307:258-269.

Cebon et al., "Granulocyte-Macrophage Colony Stimulating Factor from Human Lymphocytes. The effect of glycosylation on receptor binding and biological activity," *J. Biol. Chem.*, 1990, 265(8):4483-4491.

Cera et al., "Water-soluble polysaccharide-anthracycline conjugates: Biological Activity," *Anti-Cancer Drug Design*, 1992, 7(2):143-151.

Cerami, "Beyond Erythropoiesis: Novel Applications for Recombinant Human Erythropoietin," *Semin. Hematol.*, 2001, 38:(3 Suppl 7):33-39.

Cerny et al., "A Hydroxyethyl Starch-Hemoglobin Polymer as a Blood Substitute," *Clinical Hemorheology*, 1982, 2(4):355-365.

Cervigni et al., "Synthesis of Glycopeptides and Lipopeptides by Chemoselective Ligation," *Angewandte Chemie International Edition in English*, 1996, 35(11):1230-1232.

Chagnon et al., "Murine renal cell carcinoma: evaluation of a dendritic-cell tumour vaccine," *BJU Int.*, 2001, 88:418-424.

Chamow and Ashkenazi, *Antibody Fusion Proteins*, 1999, Wiley & Sons, Inc. (TOC Only).

Chamow et al., "Conjugation of Soluble CD4 without Loss of Biological Activity via a Novel Carbohydrate-directed Cross-linking Reagent," *J. Biol. Chem.*, 1992, 267(22):15916-15922.

Chan et al., "Preparation of O-esters from the corresponding thiol esters: *tert*-butyl cyclohexanecarboxylate," *Organic Syntheses, Coll.*, 1990, 7:87-93.

Chang, "Blood Substitutes Based on Modified Hemoglobin Prepared by Encapsulation or Crosslinking: An Overview," *Biomat. Art. Cells Immob. Biotech.*, 1992, 20:159-179.

Chaplin and Kennedy (eds.), *Carbohydrate Analysis: a practical approach*, 1996, Montreuill, "Glycoproteins," pp. 175-177; IRL Press Practical approach series.

Chaplin and Kennedy (eds.), *Carbohydrate Analysis: a practical approach*, 1994, 2nd Edition, Chapter 1 "Monosaccharides," pp. 1-41, Chapter 2 "Oligosaccharides" pp. 42-72, Chapter 3 "Neutral Polysaccharides" pp. 73-124, Chapter 5 "Glycoproteins" pp. 181-293, IRL Press.

Chaplin, "A Rapid and Sensitive Method for the Analysis of Carbohydrate Components in Glycoproteins Using Gas-Liquid Chromatography," *Anal. Biochem.*, 1982, 123:336-341.

Chaplin, "Monosaccharides," *Carbohydrate analysis: a practical approach*, 1996, Chaplin and Kennedy (eds.), Chapter 1, "Oligosaccharides," pp. 37-54.

Chapman et al., "Therapeutic antibody fragments with prolonged in vivo half-lives," *Nature Biotech.*, 1999, 17:780-783.

Chen et al., "Purification of $\alpha_1$ Proteinase Inhibitor from Human Plasma Fraction IV-1 by Ion Exchange Chromatography," *Vox Sang*, 1998, 74:232-241.

Choay et al., "Structural studies on a biologically active hexasaccharide obtained from heparin," *Ann. NY Acad. Sci.*, 1981, 370:644-649.

Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.

Chow et al., "In vitro Induction of apoptosis of neoplastic cells in low-grade non-Hodgkin's lymphomas using combinations of established cytotoxic drugs with bendamustine," *Haematologica*, 2001, 86:485-493.

Chu et al., "Further Studies on the Immunogenicity of *Haemophilus influenzae* Type b and Pneumococcal Type 6A Polysaccharide-Protein Conjugates," *Infect. Immun.*, 1983, 40:245-256.

Colman, "Production of therapeutic proteins in the milk of transgenic livestock," *Biochem. Soc. Symp.*, 1998, 63:141-147.

Conradt et al., "Expression of Human Interleukin-2 in Recombinant Baby Hamster Kidney, Ltk⁻, and Chinese Hamster Ovary Cells. Structure of O-linked carbohydrate chains and their location within the polypeptide," *J. Biol. Chem.*, 1989, 264(29):17368-17373.

Corey and Clark, "A new method for the synthesis of 2-pyridinethiol carboxylic esters," *Tetrahedron Lett.*, 1979, 31:2875-2878.

(56) References Cited

OTHER PUBLICATIONS

Cumber et al., "Preparation of Antibody-Toxin Conjugates," *Meth. Enzymol.*, 1985, 112:207-225.
Davis and Flitsch, "A Novel Method for the Specific Glycosylation of Proteins," *Tetrahedron Lett.*, 1991, 32(46):6793-6796.
de Koning et al., "An approach to the synthesis of peptide-PNA-peptide conjugates via native ligation," *Tetrahedron Lett.*, 2002, 43(45): 8173-8176.
De Velasco et al., "Synthetic Peptides Representing T-Cell Epitopes Act as Carriers in Pneumococcal Polysaccharide Conjugate Vaccines," *Infect. Immun.*, 1995, 63(3):961-968.
Definition of dimethyl sulfoxide, the Merck Index, 2006, Merck & Co., 14th edition, accessed online http://themerckindex.cambridgesoft.com/TheMerckIndex/index.asp on Sep. 4, 2007.
Delgado et al., "The Uses and Properties of PEG-Linked Proteins," *Crit. Rev. Ther. Drug Carrier Syst.*, 1992, 9(3,4):249-304.
Delorme et al., "Role of Glycosylation on the Secretion and Biological Activity of Erythropoietin," *Biochemistry*, 1992, 31(41):9871-9876.
Denzlinger et al., "Differential Activation of the Endogenous Leukotriene Biosynthesis by Two Different Preparations of Granulocyte-Macrophage Colony-Stimulating Factor in Healthy Volunteers," *Blood*, 1993, 81(8):2007-2013.
*Dictionary of Chemistry and Chemical Technology*, 2003, p. 769 (English translation provided).
Dieterich et al., "Hydroxyethyl Starch Antibodies in Humans: Incidence and Clinical Relevance," *Anesth. Analg.*, 1998, 86:1123-1126.
Dittmar et al., "Human Glycoproteins and Derived Variants from Recombinant Mammalian Cell Lines," *Advances in Protein Design*, 1989, 12:145-156.
Donahue et al., "Effects of N-linked Carbohydrates on the In Vivo Properties of Human GM-CSF," *Cold Spring Harbor Symp. Quant. Biol.*, 1986, 51:685-692.
Dorner et al., "Increased Synthesis of Secreted Proteins Induces Expression of Glucose-regulated Proteins in Butyrate-treated Chinese Hamster Ovary Cells," *J. Biol. Chem.*, 1989, 264(34):20602-20607.
Dorwald, *Side Reactions in Organic Synthesis, A Guide to Successful Synthesis Design*, 2005, Wiley-VCH Verlag GmbH & Co. Preface p. IX-X.
Dowling and Russell, "Pharmacokinetics of a long-acting oxytetracycline-polyethylene glycol formulation in horses," *J. Vet. Pharmacol. Therap.*, 2000, 23:107-110.
Dreborg and Åkerblom, "Immunotherapy with Monomethoxypolyethylene Glycol Modified Allergens," *Crit. Rev. Ther. Drug Carrier Syst.*, 1990, 6(4):315-365.
Edmunds et al., "Transgenically Produced Human Antithrombin: Structural and Functional Comparison to Human Plasma-Derived Antithrombin," *Blood*, 1998, 91(12):4561-4571.
Elliott et al., "Mapping of the Active Site of Recombinant Human Erythropoietin," *Blood*, 1997, 89(2): 493-502.
Ernst et al. (eds.), *Carbohydrates in Chemistry and Biology*, 2000, Part I, vol. 1-2, Whiley-VCH Weinheim (TOC only).
Etrych et al., "New HPMA Copolymers containing doxorubicin bound via pH-sensitive linkage: synthesis and preliminary in vitro and in vivo biological properties," *J. Controlled Release*, 2001, 73:89-102.
European Pharmacopoeia, "Erythropoietin Concentrated Solution," 3rd Edition, 2000, Monography, pp. 655-660.
European Pharmacopoeia, "Erythropoietin Concentrated Solution," 4th Edition, 2002, Monography, pp. 1123-1128.
European Pharmacopoeia, "Erythropoietin concentrated solution," *Pharmaeuropa.*, 1996, 8: 371-377.
European Pharmacopoeia, "Haemodialysis solutions, concentrated, water for diluting," 2001, 911-917.
Fernández-Santana et al., "Conjugation of 5-azido-3-oxapentyl glycosides with thiolated proteins through the use of thiophilic derivatives," *Glycoconj. J.*, 1998, 15:549-553.

Fibi et al., "Evidence for the Location of the Receptor-Binding Site of Human Erythropoietin at the Carboxyl-Terminal Domain," *Blood*, 1991, 77(6):1203-1210.
Fibi et al., "N- and O-Glycosylation Muteins of Recombinant Human Erythropoietin Secreted From BHK-21 Cells," *Blood*, 1995, 85(5):1229-1236.
Fissekis et al., "*N*-Pantyol-(substituted)amines, Pantothenic Acid Analogues," *J. Med. Pharm. Chem.*, 1960, 2:47-56.
Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271(5):907-919.
Franzen and Svensson, "Structural Studies on the Carbohydrate Portion of Human Antithrombin III," *J. Biol. Chem.*, 1980, 255(11):5090-5093.
Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.
Fujiki et al., "Studies on the disulfide bonds in human pituitary follicle-stimulating hormone," *Biochim. Biophys. Acta*, 1980, 624: 428-435.
Gaertner and Offord, "Site-Specific Attachment of Functionalized Poly(ethylene glycol) to the Amino Terminus of Proteins," *Bioconjugate Chemistry*, 1996, 7(1):38-44.
Ganson et al., "Control of Hyperuricemia in Subjects with refractory gout, and induction of antibody against poly (ethylene glycol) (PEG), in a phase 1 trial of subcutaneous PEGylated urate oxidase," *Arthritis Research and Therapy*, 2005, 8: R12.
Gaucher et al., "Stereospecific synthesis and characterization of aminoglycoside ligands from diethylenetriamine," *J. Organic Chem.*, 1999, 64:4012-4015.
Gervais et al., "NMR investigations of the role of the sugar moiety in glycosylated recombinant human granulocyte-colony-stimulating factor," *Eur. J. Biochem.*, 1997, 247:386-395.
Gerwech et al., "Tumor pH controls the in vivo efficacy of weak acid and base chemotherapeutics," *Mol. Cancer Ther.*, 2006, 5(5): 1275-1279.
Gillis et al., "T Cell Growth Factor: Parameters of Production and a Quantitative Microassay for Activity," *J. Immunol.*, 1978, 120(6):2027-2032.
Glederblom et al., "Cremophor El: the drawbacks and advantages of vehicle selection for drug formulation," *Eur. J. Cancer*, 2001, 37: 1590-1598.
Goldstein and Gelb, "An alternate preparation of thioester resin linkers for solid-phase synthesis of peptide C-terminal thioacids," *Tetrahedron Lett.*, 2000, 41(16):2797-2800.
Gonzalez et al., "Chemoenzymatic synthesis of spacer-linked oligosaccharides for the preparation of neoglycoproteins," *Carbohydr. Res.*, 1999, 317:180-190.
Goronzy et al., "T-Cell Derived Lymphokines as Regulators of Chronic Inflammation: Potential Targets for Immunomodulation?" *Am. J. Ther.*, 1996, 3(2):109-114.
Gould et al., "The Development of Hemoglobin Solutions as Red Cell Substitutes: Hemoglobin Solutions," *Transfus. Sci.*, 1995, 16:5-17.
Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.
Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.
Grabenhorst et al., "Construction of stable BHK-21 cells coexpressing human secretory glycoproteins and human Gal(β1-4)GlcNAc-R α2,6-sialyltransferase: α2,6-Linked NeuAc is preferentially attached to the Gal(β1-4)GlcNAc(β1-2)Man(α1-3)-branch of diantennary oligosaccharides from secreted recombinant β-trace protein," *Eur. J. Biochem.*, 1995, 232:718-725.

(56) References Cited

OTHER PUBLICATIONS

Grabenhorst et al., "Genetic engineering of recombinant glycoproteins and the glycosylation pathway in mammalian host cells," *Glycoconj J.*, 1999, 16(2):81-97.

Grabenhorst et al., "In Vivo Specificity of Human α1,3/4-Fucosyltansferases III-VII in the Biosynthesis of Lewis$^x$ and Sialyl Lewis$^x$ Motifs on Complex-type N-Glycans. Coexpression studies from BHK-21 cells together with human β-trace protein," *J. Biol. Chem.*, 1998, 273(47):30985-30994.

Gray, "The Direct Coupling of Oligosaccharides to Proteins and Derivatized Gels,"*Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Greenwald et al., "Drug Delivery Systems: Water Soluble Taxol 2'-Poly (ethylene glycol) Ester Prodrugs- Design and in Vivo Effectiveness" *J. Med. Chem.*, 39: 424-431 (1996).

Gribben et al., "Development of antibodies to unprotected glycosylation sites on recombinant GM-CSF," *Lancet*, 1990, 335:434-437.

Grieco et al., "Aryl selenocyanates and aryl thiocyanates: reagents for the preparation of activated esters,"*J. Org. Chem.*, 1978,43(6):1283-1285.

Grimmecke and Brade, "Studies on the reductive amination of 3-deoxy-D-*manno*-octulosonic acid (Kdo)," *Glycoconj. J.*, 1998, 15:555-562.

Guillaumie et al., "Immobilization of Pectin Fragments on solid supports: novel coupling by thiazolidine formation,"*Bioconj. Chem.*, 2002, 13:285-294.

Habeeb, "Determination of Free Amino Groups in Proteins by Trinitrobenzenesulfonic Acid," *Anal. Biochem.*, 1966, 14:328-336.

Hai et al., "Diaspirin Crosslinked Hemoglobin (DCLHb™) Polymerization," *Art. Cells, Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamilton et al., Characterization of Human Ovarian Carcinoma Cell Line (NIH: OVCAR-3) with Androgen and Estrogen Receptors, *Cancer Research*, 1983, 43: 5379-5389.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Harada et al., "Carrier and dose effects on the pharmacokinetics of T-0128, a camptothecin analogue-carboxymethyl dextran conjugate, in non-tumor-and tumor-bearing rats," *J. Controlled Release*, 2001, 71:71-86.

Harada et al., Determinants for the drug release from T-0128, camptothecin analogue-carboxymethyl dextran conjugate, *J. Controlled Release*, 2000, 69: 399-412.

Harris et al., "Pegylation. A novel process for modifying pharmacokinetics," *Clin. Pharmacokinet*, 2001, 40(7): 539-551.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of β-Lactoglobulin by Conjugation with Carboxymethyl Dextran," *Bioconjug. Chem.*, 2000, 11:84-93.

He et al., "A simplified system for generating recombinant adenoviruses," *Proc. Natl. Acad. Sci. USA*, 1998, 95:2509-2514.

Heindel et al, "Hydrazide Pharmaceuticals as Conjugates to Polyaldehyde Dextran," *Bioconjugate Chem.* 1990, 1: 77-82.

Heitzmann and Richards, "Use of the Avidin-Biotin Complex for Specific Staining of Biological Membranes in Electron Microscopy," *Proc. Natl. Acad. Sci. USA*, 1974, 71(9):3537-3561.

Herman et al., "Characterization, Formulation, and Stability of Neupogen® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of N-Glycans by High-pH Anion-Exchange Chromatography with Pulsed Amperometric Detection," *Anal. Biochem.*, 1992, 203(2):281-289.

Heterobifunctional Crosslinkers by Molecular Biosciences [http://web.archive.org/web/20011104182428 1http:/ Iwww.molbio.comlHeterobi.htm]. [Retrieved on Jun. 6, 2011].

Higuchi et al., "Role of Sugar Chains in the Expression of the Biological Activity of Human Erythropoietin," *J. Biol. Chem.*, 1992, 267(11):7703-7709.

Hodges and Chan, "Locations of Oligosaccharide Chains in Human α1-Protease Inhibitor and Oligosaccharide Structures at Each Site," *Biochemistry*, 1982, 21:2805-2810.

Hodges et al., "Structure of the Oligosaccharide Chains in Human $α_1$-Protease Inhibitor," *J. Biol. Chem.*, 1979, 254(17):8208-8212.

Hovgaard et al., "Clinical pharmacokinetic studies of a human haemopoietic growth factor, GM-CSF," *Eur. J. Clin. Inv.*, 1992, 22:45-49.

Hovinen et al., "Ethyl[2-deoxy-5-0-(4,4'-dimethoxytrityl)-α-and β-D-*erythro*-pentofuranosyl] acetates as versatile intermediates in nucleic acid chemistry," *Nucleosides Nucleotides*, 1999, 18:1263-1264.

Iakovenko et al., "Semi-synthetic Rab proteins as tools for studying intermolecular interactions," *FEBS Letters*, 2000, 468:155-158.

Ingenito et al., "Solid Phase Synthesis of Peptide C-Terminal Thioesters by Fmoc/t-Bu Chemistry," *J. Am. Chem. Soc.*, 1999, 121:11369-11374.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jaques et al., "N.M.R. spectroscopy and calcium binding of sialic acids: N-glycolylneuraminic acid and periodate-oxidized N-acetylneuraminic acid," *Carb. Res.*, 1980, 83:21-32.

Jia et al., "S-nitrosohaemoglobin: a dynamic activity of blood involved in vascular control," *Nature*, 1996, 380:221-226.

Johnson, "Oxime" from McGraw-Hill's Access Science [online], [retrieved May 9, 2011]. Retrieved from the internet <http://accessscience.com/content.aspx?searchStr=oxime&id=480600>.

Jones et al., "A convenient synthesis of N-(tert-butyloxycarbonyl)aminooxy ethers," *Tetrahedron Lett.*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Jungheinrich et al., "Pharmacokinetics of Hydroxyethyl Starch," *Clin. Pharmacokinet.*, 2005, 44 (7):681-699.

Kallin, "Coupling of Oligosaccharides to Proteins Using p-Trifluoroacetamidoaniline," *Meth. Enzymol.*, 1994, 242:119-123.

Karpusas et al., The crystal structure of human interferon β at 2.2-Å resolution, *Proc. Natl. Acad. Sci. USA*, 1997, 94:11813-11818.

Katsumi et al., "Development of Polyethylene Glycol-Conjugated Poly-S Nitrosated Serum Albumin, a Novel S-Nitrosothiol for Prolonged Delivery of Nitric Oxide in the Blood Circulation in Vivo," *J. Pharmacol. Exp. Ther.*, 2005, 314(3): 1117-1124.

Kaufman et al., "Synthesis, Processing, and Secretion of Recombinant Human Factor VIII Expressed in Mammalian Cells," *J. Biol. Chem.*, 1988, 263(13):6352-6362.

Kaushansky et al., "Role of Carbohydrate in the Function of Human Granulocyte-Macrophage Colony-Stimulating Factor," *Biochemistry*, 1987, 26:4861-4867.

Keaney, Jr. et al., "NO Forms an Adduct with Serum Albumin that Has Endothelium-derived Relaxing Factor-like Properties," *J. Clin. Invest.*, 1993, 91:1582-1589.

(56) References Cited

OTHER PUBLICATIONS

Keene et al., "Expression of Biologically Active Human Follitropin in Chinese Hamster Ovary Cells," *J. Biol. Chem.*, 1989, 264(9):4769-4775.
Keipert et al., "Functional properties of a new crosslinked hemoglobin designed for use as a red cell substitute," *Transfusion*, 1989, 29:768-773.
Kinstler et al., "Characterization and Stablility of N-terminally PEGylated rhG-CSF," *Pharmaceut. Res.*, 1996, 13(7): 996-1002.
Kitamura et al., "Chemical Engineering of the Monoclonal Antibody A7 by Polyethylene Glycol for Targeting Cancer Chemotherapy," *Cancer Res.*, 1991, 51:4310-4315.
Kitamura et al., "Establishment and Characterization of a Unique Human Cell Line That Proliferates Dependently on GM-CSF, IL-3, or Erythropoietin," *J. Cell. Phys.*, 1989, 140:323-334.
Kleine-Tebbe et al., "Allergen Immunotherapy—A Position Paper of the German Society for Allergology and Clinical Immunology," *Pneumologie*, 2001, 55:438-444 (w/English summary).
Klemm et al., "Esterification of Cellulose," *Comprehensive Cellulose Chemistry*, 1998, vol. 2, Wiley-VCH, Weinheim, New York, especially chapter 4.4, pp. 99-207.
Klimek et al., "Specific Immunotherapy (Hyposensibilisation)," *Allergologie und Umweltmedizin*, Chapter 15, pp. 157-195.
Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.
Kochendoerfer et al., "Design and Chemical Synthesis of a Homogeneous Polymer-Modified Erythropoiesis Protein," *Science*, 2003, 299(5608):884-887.
Kojima et al., "Mitomycin C-dextran conjugate: a novel high molecular weight pro-drug of mitomycin C," *J. Pharm. Pharmacol.*, 1980, 32:30-34.
Komatsu et al., "Cloning of granulocyte colony-stimulating factor cDNA from human macrophages and its expression in *Escherichia coli*," *Jpn. J. Cancer Res.*, 1987, 78(11):1179-1181.
Kraehenbuhl et al., "Preparation and characterization of an immuno-electron microscope tracer consisting of a heme-octapeptide coupled to Fab," *J. Exp. Med.*, 1974, 139:208-223.
Krantz, "Erythropoietin," *Blood*, 1991, 77(3):419-434.
Krystal et al., "Purification of Human Erythropoietin to Homogeneity by a Rapid Five-Step Procedure," *Blood*, 1986, 67(1):71-79.
Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.
Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.
Kuberan et al., "Preparation and isolation of neoglycoconjugates using biotin-streptavidin complexes," *Glycoconj. J.*, 1999, 16:271-281.
Kulicke et al., "Measurements of the Refractive Index Increment on Hydroxyethyl Starch as a Basis for Absolute Molecular Weight Determinations," *Starch*, 1991, 43(10): 392-396.
Kurtz and Eckardt, "Assays for Erythropoietin," *Nephron.*, 1989, 51(suppl 1):11-14 (w/English summary).
Lahiri et al., "Antithrombin-Heparin Cofactor: An Inhibitor of Plasma Kallikrein," *Arch. Biochem. Biophys.*, 1976, 175:737-747.
Laine et al., "Polyethylene Glycol Nephrotoxicity Secondary to Prolonged High-Dose Intravenous Lorazepam," *Ann. Pharmacother.*, 1995, 29:1110-1114.
Lapthorn et al., "Crystal structure of human chorionic gonadotropin," *Nature*, 1994, 369:455-461.
Larionova et al., "Conjugation of the Bowman-Birk Soybean Proteinase Inhibitor with Hydroxyethylstarch," *Appl. Biochem. Biotech.*, 1997, 62:175-182.
Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.
Lee et al. "Conjugation of trypsin by temperature-sensitve polymers containing a carbohydrate moiety: thermal modulation of enzyme activity," *Biotechnol. Prog.*, 1998, 14(3):508-516.
Lee et al., "Functional Polymers for Layer-by-Layer Construction of Multilayer via Chemoselective Immobilization," *Macromolecules*, 2004, 37:1849-1856.
Lee, ed., *Peptide and Protein Drug Delivery*, Marcel Dekker, 1991, p. 65.
Leenders et al., "β-Glucuronyl Carbamate Based Pro-moieties Designed for Prodrugs in ADEPT," *Tetrahedron Lett.*, 1995, 36(10):1701-1704.
Lees et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.
Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.
Levy et al., "Recombinant Antithrombin: Production and Role in Cardiovascular Disorder," *Sem. Thromb. Hem.*, 2001, 27(4):405-416.
Lewis et al., "Regiospecific 4'-O-β-glucosidation of isoflavones," *Tetrahedron Letters*, 1998, 39(51):9559-9562.
Lewis et al., "The phase transfer catalysed synthesis of isoflavone-O-glucosides," *J. Chem. Soc. Perkins Trans. 1*, 1998, 2481-2484.
Li et al., "Direct preparation of peptide thioesters using an Fmoc solid-phase method," *Tetrahedron Lett.*, 1998, 39(47):8669-8672.
Lieber et al., "A Continuous Tumor-Cell Line From a Human Lung Carcinoma with Properties of Type II Alveolar Epithelial Cells," *Int. J. Cancer*, 1976, 17: 62-70.
Lin et al., "$_L$-Cysteine as a water-soluble cation scavenger in the removal of the 2,4,6-trimethoxybenzyl group from thiols," *Tetrahedron Lett.*, 2002, 43:4531-4533.
Lin et al., "Cloning and expression of the human erythropoietin gene," *Proc. Natl. Acad. Sci. USA*, 1985, 82:7580-7584.
Lindsey at al., "Porphyrin Building Blocks for Modular Construction of Bioorganic Model Systems," *Tetrahedron*, 1994, 50(30):8941-8968.
Lipke et al., "Localized Delivery of Nitric Oxide from Hydrogels Inhibits Neointima Formation in Rat Cartoid Balloon Injury Model," *Acta Biomaterialia*, 2005, 1: 597-606.
Liu et al., "Characterization of the structural and functional changes of hemoglobin in dimethyl sulfoxide by spectroscopic techniques," *Biochim. Biophys. Acta*, 1998, 138:53-60.
Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.
Lönngren and Goldstein, "Coupling of Aldobionic Acids to Proteins Using Water-Soluble Carbodiimide," *Meth. Enzymol.*, 1994, 242:116-118.
Lund et al., "Assessment of methods for covalent binding of nucleic acids to magnetic beads, Dynabeads, and the characteristics of the bound nucleic acids in hybridization reactions," *Nucl. Acids Res.*, 1988, 16(22): 10861-10880.
Luo et al., "Controlled DNA delivery systems," *Pharm. Res.*, 1999, 16(8):1300-1308.
Manger et al., "1-*N*-Glycyl β-Oligosaccharide Derivatives as Stable Intermediates for the Formation of Glycoconjugate Probes," *Biochemistry*, 1992, 31:10724-10732.
Manger et al., "Synthesis of 1-*N*-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.
Maout et al., "Hydroxyethylstarch Conjugated to Human Hemoglobin for use in Blood Transfusion: Comparison with Dextran Conjugates," *Carbohydrates and Carbohydrate Polymers—Analysis, Biotechnology, Modification, Antiviral and Other Applications*, 1993, Chapter 12, pp. 132-140.
March, "Delocalized Chemical Bonding," *Adv. Org. Chem.*, 1992, 4th Edition, John Wiley and Sons, New York, Chapter 2 pp. 26-292.

(56) References Cited

OTHER PUBLICATIONS

Masamune et al., "A General, Selective Synthesis of Thiol Esters," *Can. J. Chem.*, 1975, 53:3693-3695.
Masamune et al., "Tylonolide Hemiacetal, the Aglycone of Tylosin, and Its Partial Synthesis," *J. Am. Chem. Soc.*, 1976, 98:7874-7875.
Masuda et al., "Synthesis and Anti-Influenza Evaluation of Orally Active Bicyclic Ether Derivatives Related to Zanamivir," *Bioorganic Med. Chem. Lett.*, 2003, 13:669-673.
McMahon et al., "Pharmacokinetics and Effects of Recombinant Human Erythropoietin After Intravenous and Subcutaneous Injections in Healthy Volunteers," *Blood*, 1990, 76(9):1718-1722.
Mega et al., "Studies on the Oligosaccharide Chains of Human $\alpha_1$-Protease Inhibitor. I. Isolation of glycopeptides," *J. Biol. Chem.*, 1980, 255(9):4053-4056.
Mega et al., "Studies on the Oligosaccharide Chains of Human $\alpha_1$-Protease Inhibitor. II. Structure of oligosaccharides," *J. Biol. Chem.*, 1980, 255(9):4057-4061.
Megson et al., "Inhibition of Human Platelet Aggregation by a Novel S-Nitrosothiol is Abolished by Hemoglobin and Red Blood Cell in vitro: Implications for Anti-Thrombotic Therapy," *Br. J. Pharmacol.*, 2000, 131: 1391-1398.
Meinjohanns et al., "Novel sequential solid-phase synthesis of N-linked glycopeptides from natural sources," *J. Chem. Soc., Perkin Trans. 1*, 1998, 1:549-560.
Menache et al., "Antithrombin III: physiology, deficiency, and replacement therapy," *Transfusion*, 1992, 32:580-588.
Menache, "Antithrombin III: Introduction," *Semin Hematol.*, 1991, 28:1-2.
Mikola and Hänninen, "Introduction of Aliphatic Amino and Hydroxy Groups to Keto Steroids Using O-Substituted Hydroxylamines," *Bioconj. Chem.*, 1992, 3(2):182-186.
Ming et al., "Interleukin 6 is the Principal Cytolytic T Lymphocyte Differentiation Factor for Thymocytes in Human Leukocyte Conditioned Medium," *J. Mol. Cell. Immunol.*, 1989, 4:203-212.
Minnema et al., "Recombinant human antithrombin III improves survival and attenuates inflammatory responses in baboons lethally challenged with *Escherichia coli*," *Blood*, 2000, 95(4):1117-1123.
Miyake et al., "Purification of Human Erythropoietin," *J. Biol. Chem.*, 1977, 252(15):5558-5564.
Montreuil et al., "Hexuronic acids," *Carbohydrate analysis: a practical approach*, 1996, Chaplin and Kennedy (eds.), Chapter 5, pp. 175-204.
Moonen et al., "Increased biological activity of deglycosylated recombinant human granulocyte/macrophage colony-stimulating factor produced by yeast or animal cells," *Proc. Natl. Acad. Sci. USA*, 1987, 84:4428-4431.
Mori et.al., "The Activation of Type 1 and Type 2 Plasminogen by Type I and Type II Tissue Plasminogen Activator," *J. Biol. Chem.*, 1995, 270(7):3261-3267.
Mosbech et al., "Hyposensitization in asthmatics with mPEG-modified and unmodified house dust mite extract," *Allergy*, 1990, 45(2):130-141.
Mosmann, "Rapid Colorimetric Assay for Cellular Growth and Survival: Application to Proliferation and Cytotoxicity Assays," *J. Immunol. Meth.*, 1983, 65:55-63.
Mueller et al., "Recombinant Glycoprotein Product Quality in Proliferation-Controlled BHK-21 Cells," *Biotechnol. Bioeng.*, 1999, 65(5):529-536.
Muir et al., "Expressed protein ligation: A general method for protein engineering," *Proc. Natl. Acad. Sci. USA*, 1998, 95:6705-6710.
Mukaiyama et al., "Peptide Synthesis *via* Oxidation-Reduction Condensation by the Use of Non-metallic Compound as a Mercaptan Scavenger," *Bull. Chem. Soc. Jpn.*, 1970, 43:1271.
Mumberg et al., "Regulatable promoters of *Saccharomyces cerevisiae*: comparison of transcriptional activity and their use for heterologous expression," *Nucl. Acids Res.*, 1994, 22(25):5767-5768.
Murano et al., "Some properties of antithrombin-III and its concentration in human plasma," *Thromb. Res.*, 1980, 18:259-262.

Nagata et al., "Molecular cloning and expression of cDNA for human granulocyte colony-stimulating factor," *Nature*, 1986, 319:415-418.
Nagata et al., "The chromosomal gene structure and two mRNAs for human granulocyte colony-stimulating factor," *EMBO J.*, 1986, 5(3):575-581.
Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.
Nathan et al., "Strategies for Covalent Attachment of Doxorubicin to Ply (PEG-Lys), a New Water Soluble Poly (etherurethane)," *J. Bioactive Compatible Polymers*, 1994, 9: 239-251.
Naundorf et al., "Characterization of two human mammary carcinomas, MT-1 and MT-3, suitable for in vivo testing of either lipids and their derivatives," *Breast Cancer Research and Treatment*, 1992, 23: 87-95.
Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.
Nimtz et al., "Carbohydrate structures of a human tissue plasminogen activator variant expressed in recombinant Chinese hamster ovary cells," *FEBS Lett.*, 1990, 271:14-18.
Nimtz et al., "Structural characterization of the oligosaccharide chains of native and crystallized boar seminal plasma spermadhesin PSP-I and PSP-II glycoforms," *Eur. J. Biochem.*, 1999, 265:703-718.
Nimtz et al., "Structures of sialylated oligosaccharides of human erythropoietin expressed in recombinant BHK-21 cells," *Eur. J. Biochem.*, 1993, 213:39-56.
Nohynek et al., "Comparison of the potency of glycosylated and nonglycosylated recombinant human granulocyte colony-stimulating factors in neutropenic and nonneutropenic CD rats," *Cancer Chemother Pharmacol.*, 1997, 39:259-266.
Nomura et al., "Pharmacokinetic characteristics and therapeutic effects of mitomycin C-dextran conjugates after intratumoural injection," *J. Controlled Release*, 1998, 52:239-252.
O'Shannessy and Wilchek, "Immobilization of Glycoconjugates by Their Oligosaccharides: Use of Hydrazido-Derivatized Matrices," *Analytical Biochemistry*, 1990, 191:1.
Ohta et al., "Usefulness of Glycopeptide Mapping by Liquid Chromatography/Mass Spectrometry in Comparability Assessment of Glycoprotein Products," *Biologicals*, 2002, 30(3):235-244.
Okamoto et al., "Purification and Characterization of Three Forms of Differently Glycosylated Recombinant Human Granulocyte-Macrophage Colony-Stimulating Factor," *Arch. Biochem. Biophys.*, 1991, 286(2):562-568.
Okamoto et al., "A facile incorporation of the aldehyde function into DNA: 3-formylindole nucleoside as an aldehyde-containing universal nucleoside," *Tetrahedron Lett.*, 2002, 43:4581-4583.
Olson and Björk, "Predominant Contribution of Surface Approximation to the Mechanism of Heparin Acceleration of the Antithrombin-Thrombin Reaction. Elucidation from salt concentration effects," *J. Biol. Chem.*, 1991, 266(10):6353-6364.
Olson et al., "Role of the Antithrombin-binding Pentasaccharide in Heparin Acceleration of Antithrombin-Proteinase Reactions. Resolution of the antithrombin conformational change contribution to heparin rate enhancement," *J. Biol. Chem.*, 1992, 267(18):12528-12538.
Opal et al., "Antithrombin, heparin, and heparan sulfate," *Crit. Care Med.*, 2002, 30(5):S325-S331.
*Organikum, Organisch-chemisches Grundpraktikum*, 1984, VEB Deutscher Verlag der Wissenschaften, p. 472 (with English translation and verification).
Pasut et al., "Antitumoral activity of PEG-gemcitabine prodrugs targeted by folic acid," *J. Controlled Release*, 2008, 127(3):239-248.
Pawlowski et al., "A new method of non-cross-linking conjugates of polysaccharides to protein via thioether bonds for the preparation of saccharide-protein conjugate vaccines," *Vaccine*, 1999, 17:1474-1483.
Pazur, "Neutral polysaccharides," *Carbohydrate analysis: a practical approach*, 1996, Chaplin and Kennedy (eds.), Chapter 3, pp. 55-96.

(56) References Cited

OTHER PUBLICATIONS

Pedley et al., "The potential for enhanced tumour localization by poly)ethylene glycol) modification of anti-CEA antibody," *Br. J. Cancer*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Pelter et al., "Synthesis of Thioesters by Reactions of Carboxylic Acids with Tris-(ethylthio)borane," *J. Am. Chem. Soc., Perkin Trans I*, 1977, 1672-674.

Peluso et al., "Asparagine surrogates for the assembly of N-linked glycopeptide mimetics by chemoselective ligation," *Tetrahedron Lett.*, 2001, 42:2085-2087.

Peri et al, "Chemo- and Stereoselective Glycosylation of Hydroxylamino Derivatives: A Versatile Approach to Glycoconjugates," *Tetrahedron*, 1998, 54, 12269-12278.

Peron et al., "Hydroxyethyl starch-induced renal insufficiency after plasma exchange in a patient with polymyositis and liver cirrhosis," *Clin. Nephrol.*, 2001, 55(5):408-411.

Peterson, *The Physiological Inhibitors of Blood Coagulation and Fibrinolysis*, 1979, Elsevier/ North-Holland Biomedical Press, p. 43.

*Pharma Business*, Jul./Aug. 2000, pp. 45-60.

Pierce Chemical Technical Library, "cross-linking," 1994, 45 pages.

Pierce Company, Crosslinking Agents, available at http://www.piercenet.com/browse.cfm?fldID=0203, printed Aug. 25, 2011.

Pike et al., "Heparin-dependent Modification of the Reactive Center Arginine of Antithrombin and Consequent Increase in Heparin Binding Affinity," *J. Biol. Chem.*, 1997, 272_32:19652-19655.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Radomsky and Temeriusz, "Thiazolidine-4(R)-carboxylic acids derived from sugars: part I, C-2-epimerisation in aqueous solutions," *Carbohydrate Res.*, 1989, 187:223-237.

Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," *Blood*, 1994, 84(12):4078-4087.

Ragupathi et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys®) for the treatment of hepatitis C," *Advanced Drug Delivery Reviews*, 2002, 54:571-586.

Reidhaar-Olson et al., "Identification of Residues Critical to the Activity of Human Granulocyte Colony-Stimulating Factor," *Biochemistry*, 1996, 35:9034-9041.

Reischl (ed)., *Molecular Diagnosis of Infectious Diseases*, 1997, vol. 13, Totowa NJ, Humana Press Inc. (TOC Only).

Relihan et al., "Clearance Rate and Effect on Renal Function of Stroma-Free Hemoglobin Following Renal Ischemia," *Ann. Surg.*, 1972, 176(6):700-704.

Revoltella et al., "Natural and Therapy-Induced Anti-GM-CSF and Anti-G-CSF Antibodies in Human Serum," *Leukemia and Lymphoma*, 1997, 26:29-34.

Reynolds et al., "S-nitrosohemoglobin deficiency: A mechanism for loss of physiological activity in banked blood," *Proc. Natl. Acad. Sci. USA*, 2007, 104(43): 17058-17062.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Riess, "Oxygen Carriers ("Blood Substitutes")—Raison d'etre, chemistry, and Some Physiology," *Chem. Rev.*, 2001, 101:2797-2919.

Rodrigues et al., "Correlation of the acid-sensitivity of polyethylene glycol daunorubicin conjugates with their in vitro anti proliferative activity," *Bioorganic Med. Chem.*, 2006, 14: 4110-4117.

Roemisch et al., "Antithrombin: a new look at the actions of a serine protease inhibitor," *Blood Coagul. Fibrinolysis*, 2002, 13:657-670.

Rogers et al., "Effects of polymerization on the oxygen carrying and redox properties of diaspirin cross-linked hemoglobin," *Biochim Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Rose, "Facile Synthesis of Homogeneous Artificial Proteins," *J. Am. Chem. Soc.*, 1994, 116:30-33.

Rosenberg et al., "Antithrombin-III," *Rev. Hematol.*, 1986, 2:351-416.

Rosenberg, "Role of heparin and heparinlike molecules in thrombosis and atherosclerosis," *Fed. Proc.*, 1985, 44:404-409.

Rotondaro et al., "Purification and Characterization of Two Recombinant Human Granulocyte Colony-Stimulating Factor Glycoforms," *Mol. Biotechnol.*, 1999, 11: 117-128.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67(8):1442-1452.

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al. "Synthesis and Physicochemical Characterization of a series of Hemoglobin-Based Oxygen Carriers: Objective Comparison between Cellular and Acellular Types," *Bioconjugate Chem.*, 2000, 11:56-64.

Salo et al., "Aminooxy Functionalized Oligonucleotides: Preparation, On-Support Derivitization and Postsynthetic Attachment to Polymer Support," *Bioconjugate Chem.*, 1999, 10: 815-823.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian J. Chem.*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnol.*, 1999, 30:17-25.

Schlesinger, "Alphaviruses—vectors for the expression of heterologous genes," *Trends Biotech.*, 1993, 11:18-22.

Schmoll et al. (eds.), "Summary of Basics of Oncology and Current Therapeutic Approaches," *Compendium for Internistic Oncology*, 1996, Table of Contents with English Summary.

(56) References Cited

OTHER PUBLICATIONS

Schneerson et al., "Preparation, characterization and immunogenicity of haemophilus influenzae type b polysaccharide-protein conjugates," *J. Exp. Med.*, 1980, 152:361-376.
Schottelius et al., "Improvement of Pharmacokinetics of Radioiodinated Tyr³-Octreotide by Conjugation with Carbohydrates," *Bioconjugate Chem.*, 2002, 13:1021-1030.
Schröter et al., "Male-specific Modification of Human CD52," *J. Biol. Chem.*, 1999, 274(42):29862-29873.
Seymour et al., "A phase 1 study of BAY 38-3441 given as a short infusion daily for five days every 3 weeks. A National Cancer Institute of Canada Clinical Trials Group Study," *Eur. J. Cancer*, 2001, 37(1): 73.
Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.
Shah et al., "Characterization of Colony-stimulating Activity Produced by Human Monocytes and Phytohemagglutinin-stimulated Lymphocytes," *Blood*, 1977, 50(5):811-821.
Shao and Tam, "Unprotected peptides as building blocks for the synthesis of peptide dendrimers with oxime, hydrazone and thiazolidine linkages," *J. Am. Chem. Soc.*, 1995, 117(14):3893-3899.
Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.
Shin et al., "Fmoc-Based Synthesis of Peptide;"Thioesters: Application to the Total Chemical Synthesis of a Glycoprotein by Native Chemical Ligation," *J. Am. Chem. Soc.*, 1999, 121:11684-11689.
Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.
Shu, "Somogyi Micro Copper Method," *Method in Carbohydride Chemistry*, 1962, 1:383-388.
Simmons et al., "Potent inhibition of HIV-1 infectivity in macrophages and lymphocytes by a novel CCR5 antagonist," *Science*, 1997, 276:276-279.
Skopp et al., "Fingerprinting of proteins cleaved in solution by cyanogen bromide," *Appl. Theoret. Electrophoresis*, 1989, 1:61-64.
Skwarczynski et al., "Paclitaxel Prodrugs Toward Smarter Delivery of Anticancer Agents," *J. Med. Chem.*, 2006, 49 (25): 7253-7269.
Snyder et al., "HbXL99α: A hemoglobin derivative that is cross-linked between the α subunits is useful as a blood substitute," *Proc. Natl. Acad. Sci. USA*, 1987, 84:7280-7284.
Sommermeyer et al., "Hydroxyethylstarch for Clinical Application: Physical and Chemical Characterisation," *Krankenhauspharmazie*, 1987, 8:271-278.
Somogyi, "Determination of reducing sugars," *Meth. Carb. Chem.*, 1962, 1:384-386.
Song et al., "Toxicity and Antitumor Activity of the Conjugate of Mitomycin C with Carboxymethyl-chitin," *Arch. Pract. Pharm.*, 1993, 53(3):141-147.
Souza et al., "Recombinant human granulocyte colony-stimulating factor: effects on normal and leukemic myeloid cells," *Science*, 1986, 232:61-65.
Soyez et al., "Biological evaluation of mitomycin C bound to a biodegradable polymeric carrier," *J. Controlled Release*, 1997, 47:71-80.
Spellman et al., "Carbohydrate Structures of Human Tissue Plasminogen Activator Expressed in Chinese Hamster Ovary Cells," *J. Biol. Chem.*, 1989, 264(24):14100-14111.
Spivak and Hogans, "The In Vivo Metabolism of Recombinant Human Erythropoietin in the Rat," *Blood*, 1989, 73:90-99.
Staab, "New Methods in Preparatory Organic Chemistry IV. Synthesis using heterocyclic amides (azolides)," *Angew. Chem.*, 1962, 74(12):407-422.

Staros, "*N*-Hydroxysulfosuccinimide Active Esters: Bis(*N*-hydroxysulfosuccinimide) Esters of Two Dicarboxylic Acids Are Hydrophilic, Membrane-Impermeant, Protein Cross-Linkers," *Biochemistry*, 1982, 21:3950-3955.
Stein et al., Development and characterisation of novel human multidrug resistant mammary carcinoma lines in vitro and in vivo, Int. J. Cancer, 72:885-891, (1997).
Stetsenko and Gait, Efficient Conjugation of Peptides to Oligonucleotides by "Native Ligation," *J. Org. Chem.*, 2000, 65:4900-4908.
Stewart et al., "Identification of the Mechanism Responsible for the Increased Fibrin Specificity of TNK-Tissue Plasminogen Activator Relative to Tissue Plasminogen Activator," *J. Biol. Chem.*, 2000, 275(14):10112-10120.
Stille et al., "Atherosclerosis as Consequence of Chronic Infection by *Chlamydia pneumoniae*," *Herz*, 1998, 23:185-192 (w/English summary).
Sunamoto and Iwamoto, "Protein-Coated and Polysaccharide-Coated Liposomes as Drug Carriers," *CRC Critical Review in Therapeutic Drug Carrier Systems*, 1986, 2:117-136.
Svenson and Lindberg, "Coupling of Acid Labile *Salmonella* Specific Oligosaccharides to Macromolecular Carriers," *J. Immunolog. Meth.*, 1979, 25: 323-335.
Svenson et al., "Oligosaccharide-Protein Conjugate: A Novel Approach for Making *Salmonella* O-Antigen Immunogens," *FEMS Microbiol. Lett.*, 1977, 1: 145-148.
Svenson, "Immunochemistry of *Salmonella* O-antigens: Preparation of an Octasaccharide-Bovine Serum Albumin Immunogen Representative of *Salmonella* Serogroup B O-Antigen and Characterization of the Antibody Response," *J. Immunol.*, 1978, 120(5): 1750-1757.
Sytkowski et al., "An Erythropoietin Fusion Protein Comprised of Identical Repeating Domains Exhibits Enhanced Biological Properties," *J. Biol. Chem.*, 1999, 274(35):24773-24778.
Sytkowski et al., "Human erythropoietin dimers with markedly enhanced in vivo activity," *Proc. Natl. Acad. Sci. USA*, 1998, 95(3):1184-1188.
Takeuchi and Kobata, "Structures and functional roles of the sugar chains of human erythropoietins," *Glycobiology*, 1991, 1(4):337-346.
Takeuchi et al., "Relationship between sugar chain structure and biological activity of recombinant human erythropoietin produced in Chinese hamster ovary cells," *Proc. Natl. Acad. Sci. USA*, 1989, 86:7819-7822.
Tam et al., "Peptide Synthesis Using Unprotected Peptides Through Orthogonal Coupling Methods," *Proc. Natl. Acad. Sci. USA*, 1995, 92:12485-12489.
Tam et al., "Soluble Dextran-Hemoglobin Complex as a Potential Blood Substitute," *Proc. Natl. Acad. Sci. USA*, 1976, 73(6):2128-2131.
Tanaka et al., "Pharmacokinetics of recombinant human granulocyte colony-stimulating factor conjugated to polyethylene glycol in rats," *Cancer Research*, 1991, 51:3710-3714.
Tebbutt, "Technology evaluation: transgenic α-1-antitrypsin (AAT), PPL Therapeutics," *Curr. Opin. Mol. Ther.*, 2000, 2(2):199-204.
Thermo Scientific Pierce "Crosslinking Technical Handbook," 48pgs. (2009).
Thim et al., "Amino Acid Sequence and Posttranslational Modification of Human Factor VII$_a$ from Plasma and Transfected Baby Hamster Kidney Cells," *Biochemistry*, 1988, 27:7785-7793.
Thomas et al., "Measuring blood volume with fluorescent-labeled hydroxyethyl starch," *Crit. Care Med.*, 2000, 28(3):627-631.
Thomas, "Carbohydrate Binding Sites," *Meth. Enzymol.*, 1977, 46:362-368.
Thorpe et al., "Blockade of the galactose-binding sites of ricin by its linkage to antibody," *Eur. J. Biochem.*, 1984, 140:63-71.
Tomasik et al., "Chemical Modification of Starch," *Adv. Carb. Chem. Biochem.*, 2004, 59:179-403.
Toole et al., "Molecular cloning of a cDNA encoding human antihaemophilic factor," *Nature*, 1984, 312:342-347.
Toyama et al., "Surface design of SPR-based immunosensor for the effective binding of antigen or antibody in the evanescent field using mixed polymer matrix," *Sensors and Actuators B*, 1998, 52:65-71.

(56) References Cited

OTHER PUBLICATIONS

Travis and Salvesen, "Human plasma proteinase inhibitors," *Ann. Rev. Biochem.*, 1983, 52:655-709.
Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-19568.
Van Patten et al., "Oxidation of Methionine Residues in Antithrombin," *J. Biol. Chem.*, 1999, 274(15):10268-10276.
Vasey et al., :Phase I Clinical and Pharmacokinetic Study of PKI [N-(2-Hydroxypropyl)methacrylamide Copolymer Doxorubicin]: First Member of a New Class of Chemotherapeutic Agents—Drug—Polymer Conjugates, *Clin. Cancer Res.*, 1999, 5:83-94.
Velasco et al., "Synthetic Peptides Representing T-Cell Epitopes Act as Carriers in Pneumococcal Polysaccharide Conjugate Vaccines," *Infection and Immunity*, 1995, 63(3):961-968.
Veronese et al., "Peptide and Protein PEGylation—A Review of Problems and Solutions," *Biomaterials*, 2001, 22(5):405-417.
Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.
Vilaseca et al., "Protein conjugates of defined structure: Synthesis and use of a new carrier molecule," *Bioconjugate Chemistry*, 1993, 4(6):515-520.
Wadhwa et al., "Immunogenicity of Granulocyte-Macrophage Colony-Stimulating Factor (GM-CSF) Products in Patients Undergoing Combination Therapy with GM-CSF," *Clin. Cancer Res.*, 1999, 5:1351-1361.
Waitzinger et al., "Pharmacokinetics and Tolerability of a New Hydroxyethyl Starch (HES) Specification [HE (130/0.4)] after Single-Dose Infusion of 6% or 10% Solutions in Healthy Volunteers," *Pharmacokinetics*, 1998, 16(2):151-160.
Wang et al., "Delivery of Antisense Oligonucleotides Using HPMA Polymer: Synthesis of a Thiol Polymer and its Conjugation to Water-soluble Molecules," *Bioconj. Chem.*, 1998, 9:749-757.
Wasley et al., "The Importance of N- and O-Linked Oligosaccharides for the Biosynthesis and In Vitro and In Vivo Biologic Activities of Erythropoietin," *Blood*, 1991, 77(12):2624-2632.
Watanabe et al., "A facile synthesis of carboxylic thiol esters from carboxylic acids and thiols," *Chem. Lett.*, 1976, 741-742.
Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.
Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).
Weisshaar et al., "NMR investigations of the N-linked oligosaccharides at individual glycosylation sites of human lutropin," *Eur. J. Biochem.*, 1991, 195:257-268.
White and Kennedy, "Oligosaccharides," *Carbohydrate analysis: a practical approach*, 1996, Chaplin and Kennedy (eds.), Chapter 2, pp. 1-36.
Whitesides et al., "Rates of Thiol-Disulfide Interchange Reactions between Mono- and Dithiols and Ellman's Reagent," *J. Org. Chem.*, 1977, 42(2):332-338.
Wilchek and Bayer, "Labeling Glycoconjugates with Hydrazide Reagents," *Meth. Enzymol.*, 1987, 138: 429-442.
Wong et al., "Analysis of carbohydrate-protein interactions with synthetic N-linked neoglycoconjugate probes," *Biochem. J.*, 1993, 296:817-825.
Wong et al., "Synthetic glycosylation of proteins using N-(β-saccharide) iodoacetamides: applications in site-specific glycosylation and solid-phase enzymic oligosaccharide synthesis," *Biochem. J.*, 1994, 300:843-850.
Wong, Chemical Dictionary Entry Concerning Carbohydrates, *Chemistry of Protein Conjugation and Cross-Linking*, 1993, CRCS, Inc., 6 pages including English-language Abstract.

Wong, *Chemistry of protein conjugation and cross-linking*, 1993, CRCS, Inc. (TOC only).
Wright et al., "High level expression of active human alpha-1-antitrypsin in the milk of transgenic sheep," *Biotechnology*, 1991, 9:830-834.
Xue and Wong; "Preparation of Conjugated Hemoglobins," *Meth. Enzymol.*, 1994, 231:308-322.
Yalpani et al., "Selective Chemical Modifications of Dextran," *J. Polymer Science: Polymer Chemistry Edition*, 1985, 23:1395-1405.
Yamaguchi et al., "Effects of site-directed removal of N-glycosylation sites in human erythropoietin on its production and biological properties," *J. Biol. Chem.*, 1991, 266(30):20434-20439.
Yang et al., "Functional Changes of Carboxymethyl Potato Starch by Conjugation with Amino Acids," *Biosci. Biotechnol. Biochem.*, 1995, 59(12):2203-2206.
Yoshida, "Glycamine Formation via Reductive Amination of Oligosaccharides with Benzylamine," *Meth. Enzymol.*, 1994, 247:55-64.
Yoshitake et al., "Nucleotide Sequence of the Gene for Human Factor IX (Antihemophilic factor B)," *Biochemistry*, 1985, 24:3736-3750.
Zalipsky, "Functionalized Poly(ethylene glycol) for Preparation of Biologically Relevant Conjugates," *Bioconjugate Chem.*, 1995, 6:150-165.
Zara et al., "A Carbohydrate-Directed Heterobifunctional Cross-Linking Reagent for the Synthesis of Immunoconjugates," *Anal. Biochem.*, 1991, 194:156-162.
Zettlmeissl et al., "Characterization of Recombinant Human Antithrombin III Synthesized in Chinese Hamster Ovary Cells," *J. Biol. Chem.*, 1989, 264 (35):21153-21159.
Zhang et al. "Thiazolidine formation as a general and site-specific conjugation method . . . " *Anal. Biochem.*, 1996, 233: 87-93.
Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," *Electrophoresis*, 1998, 19(13):2348-2355.
Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.
Zucali and Sulkowski, "Purification of human urinary erythropoietin on controlled-pore glass and silicic acid," *Exp. Hematol.*, 1985, 13(3):833-837.
Authorized Officer J-L Schwachtgen, International Search Report in PCT/EP03/02083, mailed May 21, 2003, 3 pages.
Authorized Officer J-L Schwachtgen, International Report on Patentability, PCT/EP03/02083, completed Jul. 26, 2004, 6 pages.
Blackburn and Gait (Eds)., "DNA and RNA Structure," in *Nucleic Acids in Chemistry and Biology*, 2nd Edition, 1996, Oxford University Press, pp. 15-81.
Englisch and Gauss, "Chemically modified oligonucleotides as probes and inhibitors," *Angew. Chem. Int. Ed. Engl.*,1991, 30:613-629.
Ng et al., "Pegaptanib, a targeted anti-VEGF aptamer for ocular vascular disease," *Nature Reviews*, 2005, 5:123-126.
Nielsen et al., "Sequence-selective recognition of DNA by strand displacement with a thymidine-substituted polyamide," *Science*, 1991, 254:1497-1500.
Pieve et al., "Modification of thiol functionalized aptamers by conjugation of synthetic polymers," *Bioconjugate Chemistry*, 2012, 21:169-174.
Ersdal-Badju et al., "Identification of the antithrombin III heparin binding site," *J. Biol. Chem.*, 1997, 272(31):19393-19400.
Grieco et al., "Favored reduction of α-chlorosilanes vs. α-chloroalkanes with tri-n-butyltin hydride," *J.Org.Chem*, 1978, 43(6):1285.
Chu et al., "Iodine-catalysed Michael addition of mercaptans to α,β-unsaturated ketones under solvent-free conditions," *Tetrahedron Letters*, 2005,46 (30):4971-4974.
Faith, "Aldehyde-phenol reaction products and derivatives," *JACS*, 1950, 72(2):837-839.

(56) References Cited

OTHER PUBLICATIONS

Gelbrich. "Untersuchungen zur Synthese neuartiger Cellulosematerialien durch topochemische Polymerreaktionen an mikrokristallinen Cellulosen," PhD Dissertation Paper, Vom Fachbereich Chemie, der Technischen Universitat Darmstadt, 1999, 158 pages (English abstract included).

Iranpoor et al., "Easily prepared azopyridines as potent and recyclable reagents for facile esterification reactions. AN efficient modified mitsunobu reaction," *J. Org. Chem.*, 2008, 73(13):4882-4887.

Lonngren et al., "Aldonate Coupling, A Simple Procedure for the Preparation of Carbohydrate-Protein Conjugates for Studies of Carbohydrate-Binding Proteins," *Arch. Biochem. Biophys.*, 1976, 175:661-669.

Nakazawa et al., "An efficient synthesis of naphthyl alkyl and aryl sulfides by the reaction of naphthols with alkane- and arenethiols," *Synthesis*, 1989, pp. 955-957.

Orlando, "Modification of proteins and low molecular weight substances with hydroxyethyl starch (HES)," PhD Dissertation Paper, Justus-Liebig Universitat Giessen, 2003, 191 pages.

Nouaimi et al., "Immobilization of trypsin on polyester fleece via different spacers," Enzyme and Microbial Technology, 2001, 29:567-574.

\* cited by examiner ent application is a continuation of U.S. Ser. No. 10/506,
COUPLING PROTEINS TO A MODIFIED POLYSACCHARIDE This application is a continuation of U.S. Ser. No. 10/506, 367, filed on Apr. 5, 2005, which is a National Stage application under 35 U.S.C. §371 and claims benefit under 35 U.S.C. §119(a) of International Application No. PCT/EP03/02083, having an International Filing Date of Feb. 28, 2003, which claims the benefit of priority of German Patent Application Serial No. 10209821.2 having a filing date of Mar. 6, 2002.

The rapid development in genetic engineering in recent decades has led to the new identification of a large number of genes for proteins having potential therapeutic benefits and to the possibility of producing without difficulty the corresponding gene products, pure or nearly pure in relatively large quantities, with the aid of biological expression systems.

However, it has emerged that the use of such proteins in practice, e.g., in diagnosis, therapy and for biotransformations, frequently meets with difficulties because the stability and solubility properties thereof, especially at physiological pH values, are often unsatisfactory. Two examples of such proteins are tumor necrosis factor TNF-α or interleukin-2.

Solubility problems additionally occur very frequently in the expression of glycoproteins in prokaryotic systems such as E. coli, because they are then expressed without the natural glycosylation, resulting in a considerably reduced solubility in some cases. This may make it necessary to use considerably more costly eukaryotic expression systems.

On therapeutic use in the body, many proteins are very quickly removed from the bloodstream or degraded. Systemically administered proteins having a molecular weight of more than about 70 kDa may be removed from the circulation by the reticuloendothelial system or specific interactions with cellular receptors. Smaller proteins having a molecular weight of less than about 70 kDa may in addition be removed to a large extent by the glomerular filtration in the kidney (exclusion limit about 70 kDa).

An approach followed recently to eliminate the described problems consists in coupling such problematic proteins to biocompatible polymers with good solubility in water, such as, for example, polyethylene glycol and dextran. On the one hand, it is possible by the coupling to increase the molecular weight above the threshold of 70 kDa, so that the plasma residence time of smaller proteins can be drastically increased, and on the other hand the solubility in aqueous medium can be improved by the hydrophilic polymer portion.

Further, usually beneficial effects which may be connected with coupling of proteins to such polymers are based on the masking of protease recognition sites and antigenic determinants on the protein molecule by the bound polymer. On the one hand, it is possible thereby for the therapeutic proteins substantially to escape proteolytic degradation, and on the other hand there is substantial suppression of the induction of allergenic reactions by the exogenous therapeutic protein. Beyond the increase in molecular weight, proteins are thus protected by the presence of a polymer from enzymatic degradation and, in addition, often from thermal denaturation. In many cases, the stability and in vivo half-life of the proteins is markedly increased, and the immunogenicity and antigenicity falls, thereby.

To date, most modifications have been carried out with polyethylene glycol or dextran, with PEG being generally preferred because it affords simpler products.

Dextran couplings have been described for only a few proteins such as, for example, streptokinase, plasmin, hemoglobin or aprotinin. However, dextran conjugates often show high allergenicity, presumably caused by dextran degradation products, a low metabolic stability and, in many cases, low yields in the coupling reactions. This has led to none of these dextran coupling products being approved as yet for therapeutic use in humans or animals.

Derivatizations with PEG have been carried out considerably more frequently, so that this method can now be regarded as standard for increasing the molecular weight of proteins. Some of these derivatives are in various phases of clinical trials or are already approved in the USA. PEG-hemoglobin is currently in phase III, as is a PEG adduct of superoxide dismutase (SOD), which is the protein which has been investigated most in relation to polymer couplings. PEG-coupled asparaginase is already employed in the therapy of acute lymphocytic leukemia. In 2001, PEG-interferon-α was approved for the treatment of hepatitis C patients.

On use of these PEG conjugates, however, side effects ranging from unpleasant to dangerous have also been reported, such as pruritis, hypersensitivity reactions and pancreatitis. In addition, the biological activity of the proteins after PEG coupling is often very low and the metabolism of the degradation products of PEG conjugates is still substantially unknown and possibly represents a health risk.

WO 99/49897 describes conjugates of hemoglobin which are formed by reacting the aldehyde groups of oxidatively ring-opened polysaccharides such as hydroxyethylstarch or dextran with primary amine groups of the protein. However, in this case, the employed polysaccharides act as polyfunctional reagents, resulting in a very heterogeneous product mixture with properties which are difficult to adjust.

U.S. Pat. No. 6,083,909 describes a process for coupling selectively oxidized hydroxyethylstarch to hemoglobin in DMSO. Our investigations have shown, however, that the desired product is not obtained under the stated conditions, because hemoglobin is denatured in DMSO and thus loses its biological activity.

There is thus still a need for physiologically well tolerated alternatives to dextran- or PEG-coupled proteins, with which the solubility of proteins can be improved or the plasma residence time of the proteins can be increased.

It is therefore an object of the invention to provide such alternatives and to develop simple and efficient processes for preparing such alternative protein derivatives.

This object is achieved according to the invention by hydroxyalkylstarch-protein conjugates which are characterized in that the binding interaction between the hydroxyalkylstarch molecule and the protein is based on a covalent bonding which is the result of a coupling reaction between the terminal aldehyde group, or a functional group derived from this aldehyde group by chemical reaction, of the hydroxyalkylstarch molecule and a functional group, which is able to react with this aldehyde group or functional group derived therefrom of the hydroxyalkylstarch molecule, of the protein, where the bonding resulting directly in the coupling reaction can be modified where appropriate by a further reaction to give the abovementioned covalent bonding.

The invention further includes pharmaceutical compositions which comprise these conjugates, and the use of these conjugates and compositions for the prophylactic or therapeutic treatment of the human or animal body, and methods for preparing these conjugates and compositions.

It has surprisingly been found that the reactions described above can, with a suitable choice of the conditions, be carried out in aqueous solution, thus allowing the biological activity of the proteins in many cases to be completely or partly retained.

The aqueous reaction medium for the coupling reaction is in this case preferably water or a mixture of water and an organic solvent, where the proportion of water in the mixture is at least about 70% by weight, preferably at least about 80% by weight, more preferably at least about 90% by weight.

The molar ratio of hydroxyalkylstarch (HAS) to protein in the coupling reaction is usually about 20:1 to 1:1, preferably about 5:1 to 1:1.

The remaining biological activity of the inventive hydroxyalkylstarch-protein conjugates, based on the initial activity of the protein, is usually at least 40%, preferably at least 50%, more preferably at least 70%, even more preferably at least 90%, most preferably at least 95%.

The hydroxyalkylstarch (HAS) employed according to the invention can be prepared by a known method, e.g. hydroxyalkylation of starch at the $C_2$ and/or $C_6$ position of the anhydroglucose units with alkylene oxide or 2-chloroalkanol, e.g. 2-chloroethanol (see, for example, U.S. Pat. No. 5,218,108 for the hydroxyethylation of starch), with various desired molecular weight ranges and degrees of substitution. It is also possible to employ any preparations obtainable commercially. The definition of the alkyl grouping in "hydroxyalkylstarch", as used herein, includes methyl, ethyl, isopropyl and n-propyl, with particular preference for ethyl. A substantial advantage of HES is that it is already approved by the authorities as biocompatible plasma expander and is employed clinically on a large scale.

The average molecular weight of the hydroxyalkylstarch can be in the range from about 3 kDa to several million daltons, preferably about 4 kDa to about 1000 kDa, more preferably in the range from about 4 kDa to about 50 kDa or in the range from about 70 kDa to about 1000 kDa, particularly preferably about 130 kDa. For coupling to small proteins, the average molecular weight of the hydroxyalkylstarch is preferably chosen so that the abovementioned threshold of 70 kDa is exceeded with the conjugates, whereas for coupling to large proteins the molecular weight of the hydroxyalkylstarch will preferably be in the lower region of said range. Since coupling is possible at a plurality of sites in a protein, it may also be advantageous to couple a plurality of small polymer chains, instead of one of high molecular weight. The degree of substitution (ratio of the number of modified anhydroglucose units to the number of anhydroglucose units in total) may likewise vary and will frequently be in the range from about 0.2 to 0.8, preferably about 0.3 to 0.7, more preferably about 0.5. (Note: the numbers relate to the "degree of substitution", which is between 0 and 1). The ratio of $C_2$ to $C_6$ substitution is normally in the range from 4 to 16, preferably in the range from 8 to 12.

These parameters can be adjusted by known methods. Experience with the use of hydroxyethylstarch (HES) as blood substitute has shown that the residence time of HES in the plasma depends on the molecular weight and the degree of substitution and type of substitution ($C_2$ substitution or $C_6$ substitution), with a higher molecular weight, a higher degree of substitution and a higher proportion of $C_2$ substitution increasing the residence time.

These relationships also apply to the inventive hydroxyalkylstarch-protein conjugates, so that the residence time of a particular conjugate in the plasma can be adjusted via the proportion of polysaccharide.

Hydroxyethylstarch products with an average molecular weight of 130 kDa and a degree of substitution of 0.5, and with an average molecular weight of 200 kDa and a degree of substitution of 0.25, have already been used clinically as blood substitutes and are also suitable for use in the present invention.

The protein suitable in the present invention is in principle any protein which has the necessary functional group, e.g. a free amino group, thiol group or carboxyl group, for reacting with the functional group of the HAS molecule.

A desired functional group can be introduced also by reacting the protein with a suitable, physiologically tolerated, bifunctional linker molecule. The remaining reactive functional group of the coupled-on linker molecule is then likewise regarded as "reactive functional group of the protein" for the purposes of the present invention.

Suitable linker molecules comprise at one end a grouping able to enter into a covalent bonding with a reactive functional group of the protein, e.g. an amino, thiol, or carboxyl group, and at the other end a grouping likewise able to enter into a covalent bonding with the terminal aldehyde group or a functional group derived therefrom by chemical reaction, e.g. a carboxyl group, activated carboxyl group, amino or thiol group. Between the two functional groups of the linker molecule there is a biocompatible bridging molecule of suitable length, e.g. a grouping derived from an alkane, an (oligo)alkylene glycol grouping or another suitable oligomer grouping. Preferred groupings able to react with amino groups are, for example, N-hydroxysuccinimide esters, sulfo-N-hydroxysuccinimide esters, imido esters or other activated carboxyl groups; preferred groupings able to react with thiol groups are, for example, maleimide and carboxyl groups; preferred groupings able to react with aldehyde or carboxyl groups are, for example, amino or thiol groups.

Examples of linker molecules for connecting SH and NH functions are:

| | |
|---|---|
| AMAS | (N-α(maleimidoacetoxy)succinimide ester) |
| BMPS | (N-β(maleimidopropyloxy)succinimide ester) |
| GMBS | (N-γ(maleimidobutyryloxy)succinimide ester) |
| EMCS | (N-ε(maleimidocaproyloxy)succinimide ester) |
| MBS | (m-(maleimidobenzoyl)-N-hydroxysuccinimide ester) |
| SMCC | (succinimidyl 4-(N-maleimidomethyl)cyclohexane-1-carboxylate) |
| SMPB | (succinimidyl 4-(p-maleimidophenyl)butyrate) |
| SPDP | (succinimidyl 3-(2-pyridyldithio)proprionate) |
| Sulfo-GMBS | (N-γ(maleimidobutyryloxy)sulfosuccinimide ester) |
| Sulfo-EMCS | (N-ε(maleimidocaproyloxy)sulfosuccinimide ester). |

Examples of linker molecules for connecting SH and SH functions are:

| | |
|---|---|
| BMB | (1.4-bis-maleimidobutane) |
| BMDB | (1.4-bis-maleimido-2,3-dihydroxybutane) |
| BMH | (bis-maleimidohexane) |
| BMOE | (bis-maleimidoethane) |
| DTME | (dithio-bis-maleimidoethane) |
| HBVS | (1.6-hexane-bis-vinyl sulfone) |
| BM(PEO)$_3$ | (1.8-bis-maleimidotriethylene glycol) |
| BM(PEO)$_4$ | (1.11-bis-maleimidotetraethylene glycol). |

Examples of linker molecules for connecting NH and NH functions are:

| | |
|---|---|
| BSOCOES | (bis-(2-succinimidyloxycarbonyloxy)ethyl) sulfone |
| BS$^3$ | (bis-(sulfosuccinimidyl) suberate) |
| DFDNB | (1.5-difluoro-2,4-nitrobenzene) |
| DMA | (dimethyl adipimidate HCl)) |
| DSG | (disuccinimidyl glutarate) |
| DSS | (disuccinimidyl suberate) |
| EGS | (ethylene glycol bis(succinimidyl succinate). |

Examples of linker molecules for connecting SH and CHO functions are:

| | |
|---|---|
| BMPH | (N-(β-maleimidopropionic acid)hydrazide TFA) |
| EMCA | (N-(ε-maleimidocaproic acid)hydrazide) |
| KMUH | (N-(κ-maleimidoundecanoic acid)hydrazide) |
| M₂C₂H | (4-(N-maleimidomethyl)cyclohexane-1-carboxylhydrazide HCl) |
| MPBH | (4-(4-N-maleimidophenyl)butyric acid hydrazide HCl) |
| PDPH | (3-(2-pyridyldithio)propionylhydrazide). |

An example of a linker molecule for connecting SH and OH functions is PMPI (N-(p-maleimidophenyl)isocyanate).

Examples of linker molecules for converting an SH function into a COOH function are:

| | |
|---|---|
| BMPA | (N-β-maleimidopropionic acid) |
| EMCH | (N-β-maleimidocaproic acid) |
| KMUA | (N-κ-maleimidoundecanoic acid). |

Examples of linker molecules for converting an NH function into a COOH function are MSA (methyl N-succinimidyl adipate) or longer-chain homologues thereof or corresponding derivatives of ethylene glycol.

Examples of linker molecules for converting a COOH function into an NH function are DAB (1,4-diaminobutane) or longer-chain homologues thereof or corresponding derivatives of ethylene glycol.

An example of a linker molecule which reacts with an amino group of a molecule and provides a protected amino group at a larger distance from this molecule to avoid steric hindrance is TFCS(N-ε(trifluoroacetylcaproyloxy)succinimide ester).

Further suitable linker molecules are known to skilled workers and commercially available or can be designed as required and depending on the functional groups present and desired in the HAS and the protein to be coupled on, and be prepared by known methods.

The term "protein" for the purposes of the present invention is intended to include every amino acid sequence which comprises at least 9-12 amino acids, preferably at least 15 amino acids, more preferably at least 25 amino acids, particularly preferably at least 50 amino acids, and also include natural derivatives, e.g. pre or proforms, glycoproteins, phosphoproteins, or synthetic modified derivatives, e.g. fusion proteins, neoglycoproteins, or proteins modified by genetic engineering methods, e.g. fusion proteins, proteins with amino acid exchanges to introduce preferred coupling sites.

For the prophylactic or therapeutic treatment of the human or animal body, the relevant protein will carry out a particular desired function in the body. The protein therefore preferably has, for example, a regulatory or catalytic function, a signal transmitting or transport function or a function in the immune response or induction of an immune response.

The protein may be selected for example from the group composed of enzymes, antibodies, antigens, transport proteins, bioadhesion proteins, hormones, growth factors, cytokines, receptors, suppressors, activators, inhibitors or a functional derivative or fragment thereof. "Functional derivative or fragment" means in this connection a derivative or fragment which has retained a desired biological property or activity of the parent molecule in whole or in part, e.g. to the extent of at least 10-30%, preferably more than 50%, even more preferably more than 70%, most preferably more than 90%. Particularly preferred examples of such a fragment are antibody fragments.

Specific examples are α-, β- or γ-interferon, interleukins, e.g. IL-1 to IL-18, growth factors, e.g. epidermal growth factor (EGF), platelet growth factor (PDGF), fibroblast growth factor (FGF), brain-derived growth factor (BDGF), nerve growth factor (NGF), B-cell growth factor (BCGF), brain-derived neurotrophic growth factor (BDNF), ciliary neurotrophic factor (CNTF), transforming growth factors, e.g. TGF-α or TGF-β, colony-stimulating factors (CSF), e.g. GM-CSF, G-CSF, BMP (bone morphogenic proteins), growth hormones, e.g. human growth hormone, tumor necrosis factors, e.g. TNF-α or TNF-β, somatostatin, somatotropin, somatomedins, serum proteins, e.g. clotting factors II-XIII, albumin, erythropoietin, myoglobin, hemoglobin, plasminogen activators, e.g. tissue plasminogen activator, hormones or prohormones, e.g. insulin, gonadotropin, melanocyte-stimulating hormone (α-MSH), triptorelin, hypothalamus hormones, e.g. antidiuretic hormones (ADH) and oxytocin, and liberins and statins, parathyroid hormone, thyroid hormones, e.g. thyroxine, thyrotropin, thyroliberin, prolactin, calcitonin, glucagon, glucagon-like peptides (GLP-1, GLP-2, etc.), exendins, e.g. exendin-4, leptin, vasopressin, gastrin, secretin, integrins, glycoprotein hormones (e.g. LH, FSH, etc.), pigmentary hormones, lipoproteins and apolipoproteins, e.g. Apo-B, Apo-E, Apo-L$_a$, immunoglobulins, e.g. IgG, IgE, IgM, IgA, IgD or a fragment thereof, hirudin, tissue pathway inhibitor, plant proteins, e.g. lectin or ricin, bee venom, snake venoms, immunotoxins, antigen E, butroxobina, alpha-proteinase inhibitor, ragweed allergen, melanin, oligolysine proteins, RGD proteins or, where appropriate, corresponding receptors for one of these proteins; or a functional derivative or fragment of one of these proteins or receptors.

Suitable enzymes may be selected for example from the groups of carbohydrate-specific enzymes, proteolytic enzymes, oxidases, oxidoreductases, transferases, hydrolases, lyases, isomerases, kinases and ligases. Specific, non-restrictive examples are asparaginase, arginase, arginine deaminase, adenosine deaminase, glutaminase, glutaminase-asparaginase, phenylalanine ammonia-lyase, tryptophanase, tyrosinase, superoxide dismutase, an endotoxinase, a catalase, peroxidase, kallikrein, trypsin, chymotrypsin, elastase, thermolysin, a lipase, a uricase, adenosine diphosphatase, purine-nucleoside phosphorylase, bilirubin oxidase, a glucose oxidase, glucodase, gluconate oxidase, galactosidase, glucocerebrosidase, glucuronidase, hyaluronidase, tissue factor, a tissue plasminogen activator, streptokinase, urokinase, MAP kinases, DNAses, RNAses, lactoferrin, and functional derivatives or fragments thereof.

As mentioned above, the functional group of the HAS molecule involved in the coupling reaction is the terminal aldehyde group or a group derived therefrom by chemical reaction.

One example of such a chemical reaction is the selective oxidation of this aldehyde group with a mild oxidizing agent such as, for example, iodine, bromine or some metal ions, or else by means of electrochemical oxidation to a carboxyl group or activated carboxyl group, e.g. an ester, lactone, amide, with the carboxyl group being converted where appropriate in a second reaction into the activated derivative. This carboxyl group or activated carboxyl group can then be coupled to a primary amino or thiol group of the protein to form an amide linkage or thioester linkage.

In a particularly preferred preparation method, this aldehyde group is selectively oxidized with a molar excess of iodine, preferably in a molar ratio of iodine to HAS of from 2:1 to 20:1, particularly preferably about 5:1 to 6:1, in aqueous basic solution. In the optimized method described in example 1, initially an amount of hydroxyalkylstarch is dissolved in hot distilled water, and somewhat less than 1 mole equivalent of aqueous iodine solution, preferably in a concentration of about 0.05-0.5N, particularly preferably about 0.1N, is added. After this, an aqueous NaOH solution in a molar concentration which is about 5-15 times, preferably about 10 times, that of the iodine solution is slowly added dropwise, at intervals of a plurality of minutes, to the reaction solution until the solution starts to become clear again after the addition. Somewhat less than 1 mole equivalent of the above aqueous iodine solution is again added to the reaction solution, the dropwise addition of the NaOH solution is resumed, and the addition of iodine and NaOH are repeated until approximately 5.5-6 mole equivalents of iodine solution and 11-12 mole equivalents of NaOH solution, based on the hydroxyalkylstarch, have been added. The reaction is then stopped, the reaction solution is desalted, e.g. by dialysis or ultrafiltration, subjected to a cation exchange chromatography, and the reaction product is obtained by lyophilization. In this method, virtually quantitative yields are achieved irrespective of the molecular weight of the HAS.

In a further particularly preferred embodiment, the selective oxidation takes place with alkaline stabilized solutions of metal ions, e.g. $Cu^{++}$ or $Ag^+$, likewise in approximately quantitative yields (example 2). It is preferred in this case to employ an approximately 3-10 times molar excess of the oxidizing agent.

The selectively oxidized hydroxyalkylstarch (ox-HAS) which has been formed is subsequently reacted in the presence of an activating reagent with a free amino group of the desired protein to form an amide linkage. Examples of suitable activating reagents are N-hydroxysuccinimide, N-hydroxyphthalimide, thiophenol, p-nitrophenol, o,p-dinitrophenol, trichlorophenol, trifluorophenol, pentachlorophenol, pentafluorophenol, 1-hydroxy-1H-benzotriazole (HOBt), HOOBt, HNSA, 2-hydroxypyridine, 3-hydroxypyridine, 3,4-dihydro-4-oxobenzotriazin-3-ol, 4-hydroxy-2,5-diphenyl-3(2H)-thiophenone 1,1-dioxide, 3-phenyl-1-(p-nitrophenyl)-2-pyrazolin-5-one), [1-benzotriazolyl-N-oxytris(dimethylamino)phosphonium hexafluorophosphate] (BOP), [1-benzotriazolyloxytripyrrolidinophosphonium hexafluorophosphate (PyBOP), [O-(benzotriazol-1-yl)-N,N,N',N'-tetramethyluronium hexafluorophosphate (HBTU), [O-(benzotriazol-1-yl)-N,N,N',N'-tetramethyluronium tetrafluoroborate (TBTU), [O-(benzotriazol-1-yl)-N,N,N',N'-bis(pentamethylene)uronium hexafluorophosphate, [O-(benzotriazol-1-yl)-N,N,N',N'-bis(tetramethylene)uronium hexafluorophosphate, carbonyldiimidazole (CDI), or preferably carbodiimides, e.g. 1-(3-dimethylaminopropyl)-3-ethylcarbodiimide (EDC), dicyclohexylcarbodiimide (DCC), diisopropylcarbodiimide (DIPC), particularly preferably EDC. In contrast to conventional methods described in the literature for similar coupling reactions, it has surprisingly been found in this connection that on use of a carbodiimide as a rule the use of otherwise obligatory further activators such as triazoles, e.g. HOBt, is unnecessary or even makes the yields worse. In the inventive coupling of ox-HES to various model compounds in the presence of EDC and absence of HOBt by contrast it was possible to achieve high yields substantially irrespective of the molecular weight of the HES (see examples).

Instead of the reaction of the carboxyl group or activated carboxyl group with a free primary amino group of the protein (e.g. of a lysine or arginine residue), an analogous reaction with a thiol group (of a cysteine) of the protein is also possible in principle. However, it must be taken into account in this connection that cysteines are usually involved in S—S bridges and are therefore not available for a coupling reaction. If, on the other hand, free cysteines are present, they frequently play an important part in catalysis or are involved in the contact site of subunits. A modification of these cysteines will then result in partial or complete loss of the biological activity. This problem could be eliminated by introducing free cysteines by conventional genetic engineering methods such as, for example directed mutagenesis or chemical peptide synthesis at those sites in the protein which are known to play no part in the activity. Optimal control of the coupling site is possible in this way. Targeted introduction of other reaction amino acids, e.g. Lys, His, Arg, Asp, Glu, into the protein would also be possible in the same way.

The reactive group of the hydroxyalkylstarch molecule can also be an amine or thiol group produced by chemical reaction of the terminal aldehyde group. For example, a reductive amination of the aldehyde group can be carried out by reaction with ammonia in the presence of hydrogen and a catalyst or in the presence of sodium cyanoborohydride. The resulting amino or thiol group can then react with a free carboxyl group of the protein (e.g. of an optionally activated glutamic or aspartic acid) to form an amide or thioester linkage.

A further possibility is for the terminal aldehyde group of the hydroxyalkylstarch molecule or a functional group derived therefrom by chemical reaction also to be reacted with a suitable physiologically tolerated bifunctional linker molecule. In this case, the "functional group derived from the terminal aldehyde group of the hydroxyalkylstarch molecule by chemical reaction" for the coupling reaction is the remaining reactive functional group of the bifunctional linker molecule with which the terminal aldehyde group or the functional group derived therefrom has been reacted. It is possible in this way likewise to convert the terminal aldehyde group into a desired functional group.

Suitable linker molecules comprise at one end a group able to enter into a covalent bonding with the terminal aldehyde group or a functional group derived therefrom by chemical reaction, e.g. a carboxyl group, activated carboxyl group, amino or thiol group, and at the other end a group able to enter into a covalent bonding with a reactive functional group of the protein, e.g. an amino, thiol or carboxyl group. Between the two functional groups of the linker molecule there is a biocompatible bridging molecule of suitable length, e.g. a grouping derived from an alkane, an (oligo)alkylene glycol grouping or another suitable oligomer grouping. Preferred groupings able to react with amino groups are, for example, N-hydroxysuccinimide esters, sulfo-N-hydroxysuccinimide esters, imido esters or other activated carboxyl groups; preferred groupings able to react with thiol groups are, for example, maleimide and carboxyl groups; preferred groupings able to react with aldehyde or carboxyl groups are, for example, amino or thiol groups.

A number of specific, non-restrictive examples of suitable linker molecules have already been indicated above with reference to the conjugation of linker molecules to the protein.

In an alternative inventive coupling method of the present invention, the terminal aldehyde group is reacted directly with a primary amino group (e.g. of a lysine or arginine residue or of the N-terminus) of the protein to form a Schiff's base. The formed Schiff's base is, subsequent or parallel thereto, reduced by reaction with a suitable reducing agent, resulting in a bonding which is stable in aqueous medium between protein and HAS. Preferred reducing agents are sodium borohydride, sodium cyanoborohydride, organic boron complexes, e.g. a 4-(dimethylamino)pyridine-boron complex, N-ethyldiiso-propylamine-boron complex, N-ethylmorpholine-boron complex, N-methylmorpholine-boron complex, N-phenylmorpholine-boron complex, lutidine-boron complex, triethylamine-boron complex, trimethylamineboron complex; suitable stereoselective reducing agents are, for example, sodium triacetate borohydride, sodium triethylborohydride, sodium trimethoxyborohydride, potassium tri-sec-butylborohydride (K-Selectride), sodium tri-sec-butylborohydride (N-Selectride), lithium tri-sec-butylborohydride (L-Selectride), potassium triamylborohydride (KS-Selectride) and lithium triamylborohydride (LS-selectride).

The yields can be improved by suitable variation of the reaction conditions. Parameters for such optimization tests are the pH of the reaction mixture (possible protein degradation by alkaline borohydride), temperature and duration of the incubation, and nature of the reducing agent for the one-pot reaction. A further alternative is the possibility of carrying out the reaction in two steps, in which case an immobilized reducing agent can be employed for the reduction step.

The products of the coupling reaction can be investigated by known methods, and the coupling efficiency can be established. Thus, for example, the free primary amino groups in the protein can be determined before and after the coupling with trinitrobenzenesulfonic acid (Habeeb, ASAF, Anal. Biochem. 14, 328-336 (1966)). The coupling yield of reactions involving primary amines could also be established by derivatization of the unreactive amines with fluorescamine and determination of the fluorescence. The molecular weight distribution can be established by SDS-PAGE and gel permeation. The protein content in the conjugate can be detected by SDS-PAGE and subsequent silver staining, while the saccharide content can be established by a glycan-specific staining of the bands separated by SDS-PAGE after blotting onto a membrane. Quantitative glycan determination is also possible. Exact identification of the coupling site on the protein is possible by peptide mapping and/or MALDI-TOF mass spectroscopy or electrospray ionization mass spectroscopy. It is possible in this way to optimize the coupling and to predetermine the molecular weight distribution and possibly (e.g. if the reactive groups on the protein differ in reactivity) even the coupling site of the products.

The conjugates of the present invention can where appropriate be employed as such or in the form of a pharmaceutical composition for the prophylactic or therapeutic treatment of the human or animal body.

Compositions of this type include a pharmaceutically effective amount of a conjugate of the invention as active ingredient, and a pharmaceutically suitable carrier and, where appropriate, other therapeutic or pharmaceutical ingredients or excipients. Excipients may include for example diluents, buffers, flavorings, binders, surface-active agents, thickeners, lubricants, preservatives (including antioxidants) and substances which serve to make the formulation isotonic with the blood of the intended recipient. A pharmaceutically effective amount is the amount sufficient to display on single or multiple administration a desired beneficial effect during a treatment to alleviate, cure or prevent a pathological condition. A pharmaceutically acceptable carrier is a carrier which is compatible both with the active pharmaceutical ingredient and with the patient's body.

The form of the composition will vary depending on the desired or suitable administration route. A preferred route is parenteral administration, e.g. subcutaneous, intramuscular, intravenous, intraarterial, intraarticular, intrathecal, extradural injection or, where appropriate, infusion. Intranasal, intratracheal or topical administration is also possible. Topical administration of growth factors conjugated according to the invention might for example speed up wound healing. The pharmaceutical compositions may beneficially be supplied in the form of a dosage unit and be produced by any method well known in the pharmacy sector.

The conjugates of the present invention can also be employed in all other sectors in which other protein-polymer conjugates, e.g. PEG-protein conjugates, have been used. Some specific, non-restrictive examples are the use of an HAS-protein conjugate as immobilized catalyst or reactant for a reaction in heterogeneous phase or as a column material for (immuno)affinity chromatography. Further possible uses will be plainly evident to the skilled worker with knowledge of the properties disclosed herein of the inventive HAS-protein conjugates.

The following examples are intended to explain the invention in more detail without, however, restricting it thereto. In particular, analogous reactions can also be carried out with hydroxymethylstarch and hydroxypropylstarch, and similar results can be achieved.

EXAMPLE 1

Selective Oxidation of Hydroxyethylstarch (HES) with Iodine 10 g of HES-130 kDa were dissolved in 12 ml of deionized water by heating in a round-bottomed flask. 2 ml of an 12 solution (0.1N) were added to this solution. A pipette with 2 ml of 1.0N NaOH was connected to the flask via a 2-way connector, and the NaOH solution was added dropwise at about 1 drop every 4 minutes. The solution was decolorized after addition of approximately 0.2 ml of the NaOH solution and, at this time, a second portion of 2 ml of 0.1N iodine solution was added. The reaction was complete after addition of a total of 14 ml of iodine solution and 2.8 ml of NaOH solution. The reaction mixture was then dialyzed against deionized water.

Lactonization:

The partially desalted solution was subjected to a chromatography on a cation exchange column (Amberlite IR-120, H$^+$ form) in order to convert the aldonate groups into aldonic acid groups. Subsequently, the water was removed by lyophilization, and thus the lactone form was obtained.

Determination of the Degree of Oxidation:

1 ml of alkaline copper reagent (3.5 g of $Na_2PO_4$, 4.0 g of K Na tatrate in 50 ml of $H_2O$, plus 10 ml of 1N NaOH, 8.0 ml of 10% strength (weight/volume) $CuSO_4$ solution and 0.089 g of K iodate in 10 ml of $H_2O$, after addition of 18 g of Na sulfate, make up to 100 ml) are pipetted in each case into 1 ml of sample solution under an $N_2$ atmosphere. The mixture is heated at 100° C. for 45 minutes. After cooling, 0.2 ml of 2.5% strength KI solution and 0.15 ml of 1M $H_2SO_4$ are added. After 5 min, 1 drop of phenol red indicator solution (1% weight/volume) is added, and titration is carried out with 5 mM $Na_2S_2O_3$ solution until the color disappears. The concentration of unreacted aldehyde groups can be calculated from the consumption of titrant.

An approximately quantitative yield was achieved (>98%). It is possible by this procedure to oxidize hydroxyethylstarches with higher molecular weight (e.g. 130 kDa, 250 kDa, 400 kDa) just like hydroxyethylstarches with lower molecular weight (e.g. 10 kDa, 25 kDa, 40 kDa), in similarly high yields.

EXAMPLE 2

Selective Oxidation of HES with $Cu^{2+}$ Ions

A solution of 0.24 mmol of HES-130 kDa was prepared in 10 ml of deionized water with heating. This solution was heated in a 100 ml round-bottomed flask to a temperature of 70-80° C., and 1.17 mmol of stabilized $Cu^{2+}$ (e.g. Rochelle salt as stabilizer or other stabilizers) and dilute aqueous NaOH solution was added (final concentration 0.1N NaOH). The temperature was then raised to 100° C., and the reaction was allowed to proceed until a reddish color had appeared. The reaction was stopped and the reaction mixture was cooled to 4° C. The reddish precipitate was removed by filtration. The filtrate was dialyzed against deionized water and then converted into the lactone as in example 1 and lyophilized. The oxidation took place quantitatively (yield>99%). It was also possible by this method to oxidize low molecular weight HES (e.g. HES-10 kDa, HES-25 kDa, HES-40 kDa) and higher molecular weight HES species.

EXAMPLE 3

Coupling of Selectively Oxidized High Molecular Weight HES (ox-HES-130 kDa) to Human Serum Albumin (HSA)

4.3 g of ox-HES-130 kDa and 200 mg of HSA (Sigma, Taufkirchen) were completely dissolved in water by gentle heating in a round-bottom flask with magnetic stirrer. 30 mg of ethyldimethylaminopropylcarbodiimide (EDC), dissolved in water, were added to this solution. After stirring very moderately for 2 h, a second portion of 30 mg of EDC was added. After stirring very moderately for a further two hours, a third portion of 40 mg of the carbodiimide was added. The reaction mixture was left under these conditions overnight, dialyzed against distilled water for 15 h and lyophilized. The success of the coupling was demonstrated by gel permeation chromatography, SDS-PAGE and carbohydrate-specific staining (Glyco-Dig kit from Roche-Boehringer, Basle) after blotting onto a PVDF membrane. The yield of coupling product was about 90%.

EXAMPLE 4

Coupling of Selectively Oxidized Low Molecular Weight HES (ox-HES-10 kDa) to Human Serum Albumin (HSA)

7.4 g of ox-HES-10 kDa and 50 mg of HSA were completely dissolved in water in a round-bottom flask with magnetic stirrer. The reaction was carried out by the method described above for high molecular weight HES, adding a total of 282 mg of EDC in three aliquots. The reaction mixture was likewise dialyzed and lyophilized as described above. Analysis (as above) showed the coupling product was obtained, but the yields were somewhat lower than in the coupling with high molecular weight ox-HES.

EXAMPLE 5

Coupling of ox-HES-130 kDa to Myoglobin (Mb)

4.3 g of ox-HES-130 kDa were completely dissolved in water (6-7 ml), and then 100 mg of Mb (Sigma, Taufkirchen), dissolved in 10 ml of 0.1M phosphate buffer (pH 7.0), were added. The coupling reaction was started by adding 30 mg of EDC. Addition of EDC was repeated every 2 hours until a total of 90 mg of the carbodiimide had been consumed. The reaction mixture was then dialyzed against 50 mM phosphate buffer, pH 7.0, and lyophilized. GPC showed a definite product peak, which was detected in the hold-up volume at 450 nm. It was possible to calculate a coupling yield of 88% from this. The oxygen-binding capacity of the hesylated myoglobin was about 76% of the binding capacity of unmodified Mb.

EXAMPLE 6

Coupling of ox-HES-10 kDa to Superoxide Dismutase (SOD)

One part by volume of an aqueous solution of ox-HES-10 kDa (1.05 g/ml) was incubated with one part by volume of a 7 mg/ml SOD solution (Sigma, Taufkirchen) in 50 mM phosphate buffer, pH 7.6, at room temperature. The coupling reaction was initiated by adding 280 mg of EDC in 5 portions over a period of 24 h. The progress of the reaction was followed by GPC analysis in phosphate buffer and detection at 280 nm. After 24 h, 81% of the protein were found in the higher molecular weight region of the separating column, and the reaction was stopped after this time. The reaction mixture was subjected to a diafiltration with a 30 kDa membrane and then lyophilized. Mass spectrometric analysis of the product showed an average molar ratio of HES to protein of about 3:1.

EXAMPLE 7

Coupling of ox-HES-130 kDa to Streptokinase (SK)

3.8 kg of ox-HES-130 kDa were dissolved together with 35 mg of streptokinase (Sigma, Taufkirchen) in the minimum amount of 50 mM phosphate buffer, pH 7.2. At room temperature, 46.5 mg of EDC and 20 mg of 1-hydroxybenzotriazole hydrate (HOBt) were added, and reaction was maintained with gentle stirring for a total of 24 h. After dialysis and freeze drying, about 78% of the protein were found as HES conjugate by GPC analysis. In the SDS-PAGE with silver staining, a distinct increase in the molecular mass of the streptokinase was observable. In parallel with this, carbohydrate structures were unambiguously detectable in the high molecular waveband with the digoxigenin method.

EXAMPLE 8

Coupling of ox-HES-130 kDa to Human Interleukin-1 (IL-2)

45 mg of ox-HES-130 kDa were completely dissolved in 0.5 ml of 50 mM Na phosphate buffer, pH 6.5, with gentle heating. After addition of 0.25 mg of human IL-2 (Sigma, Taufkirchen), which made the solution opaque, the mixture was stirred at room temperature for 4-6 h. Then 5 mg of EDC were added in 4 portions with a time difference of 2 h for each, and stirring was continued overnight, resulting in a clear solution. GPC analysis revealed a coupling yield of about 65%.

EXAMPLE 9

Coupling of ox-HES-25 kDa to Human Tumor Necrosis Factor α (TNFα)

0.3 mg of hTNFα (Sigma, Taufkirchen) were added to 86 mg of ox-HES-25 kDa in about 0.4 ml of 0.1M phosphate buffer (pH 7.0). The cloudy solution was stirred for about 2 h before 1 mg of EDC and 0.5 mg of HOBt were added. Stirring was continued for about 6 h, with the solution becoming clear during the reaction time. The coupling product was isolated by ultrafiltration and freeze drying and analyzed by GPC and detection at 280 nm. A coupling yield of approximately 74% was found in this case.

EXAMPLE 10

Coupling of ox-HES-130 kDa to Glucagon-Like Peptide (GLP-1)

7.4 g of ox-HES-130 kDa were dissolved in a minimum volume of water by heating and gentle stirring. A solution of 10 mg of GLP-1 in the amide form (Bachem, Switzerland) in 50 mM phosphate buffer, pH 7.4, was added by pipette. The reaction was started by adding 35 mg of EDC and was cautiously stirred for 2 h. This was repeated 2× more because, after this time, a peptide peak was no longer evident in the GPC analysis at 280 nm, i.e. approximately complete conversion to the coupling product had taken place. This coupling product was diafiltered using a 30 kDa membrane and lyophilized from phosphate buffer solution. It was possible to conclude from the results of a MALDI mass spectroscopy that the stoichiometry between peptide and HES was 1:1.

EXAMPLE 11

Coupling of High Molecular Weight HES (HES-130 kDa) to Human Serum Albumin (HSA)

9.75 g of HES-130 kDa were completely dissolved in water (6-7 ml), and then 50 mg of HSA, dissolved in 1 ml of 0.1M phosphate buffer (pH 7.4) were added. The reaction mixture was stirred with a magnetic stirrer. The solution was then mixed with $NaBH_3CN$ (50-70 mg) and stirred gently for a few minutes. The solution was further stirred for 15 minutes every two hours. Then a further aliquot of $NaBH_3CN$ (about 50 mg) was added. At the end (after a reaction time of almost 36 h), a total amount of 285 mg of $NaBH_3CN$ had been employed. The solution was then dialyzed and lyophilized. Analysis took place as described in example 4. The coupling efficiency was about 65%.

EXAMPLE 12

Coupling of Low Molecular Weight HES (HES-10 kDa) to Human Serum Albumin (HSA)

4.5 g of HES were completely dissolved in water (4-5 ml) and 50 mg of HSA, dissolved in 1 ml of 0.1M phosphate buffer (pH 7.4) were added. When the solution was clear, if necessary effected by stirring with a magnetic stirrer, $NaBH_4$ (50-70 mg) was added and mixed in with gentle stirring. The solution was left to stand without stirring for two hours and then stirred for 15 minutes every two hours as for the reaction with high molecular weight HES. When the solution no longer showed any bubbles ($H_2$ evolution), a further aliquot of $NaBH_4$ (about 50 mg) was added. At the end, a total amount of 180 mg of $NaBH_4$ had been employed. The solution was then dialyzed and lyophilized. Analysis took place by gel permeation chromatography (GPC), and the yield was about 15%.

EXAMPLE 13

Coupling of HES-40 kDa to Asparaginase 3.0 g of HES-40 kDa were completely dissolved in water (about 4 ml). A solution of 80 mg of asparaginase (Sigma, Taufkirchen) in 6 ml of 0.1M borate buffer, pH 9.0, were added thereto and stirred until the reaction mixture was clear. The temperature was then raised to 37° C. and, after 2 h, about 50 mg of $NaBH_3CN$ were added. This reaction cycle was repeated 3× more. The product was worked up by dialyzing the reaction mixture against 0.1M phosphate buffer, pH 7.4. The yield of coupling product was about 61%, and about 73% of the asparaginase activity was recoverable.

EXAMPLE 14

Coupling of HES-130 kDa to Human Interleukin-2 (IL-2)

50 mg of HES-130 kDa were completely dissolved in water (about 0.2 ml). A suspension of 0.25 mg of human IL-2 (Sigma, Taufkirchen) in 0.2 ml of 0.1M borate buffer, pH 9.0, was added thereto and stirred until the reaction mixture was clear (4 h). 1 mg portions of $NaBH_3CN$ were added at intervals each of 4 h, and stirring was continued. After a further reaction time of 24 h, the mixture was dialyzed against 0.1M phosphate buffer, pH 7.4 and lyophilized. The yield of coupling product was about 42% according to GPC analysis.

EXAMPLE 15

Coupling of HES-130 kDa to Insulin 4.0 g of HES-130 kDa were completely dissolved in water (about 6 ml). 55 mg of insulin from bovine pancreas (Sigma, Taufkirchen) in 7.5 ml of 0.1M borate buffer (pH 9.0), were added thereto and stirred at 37° C. for about 24 h. The reducing agent $NaBH_3CN$ (60 mg in 30 ml) was slowly added dropwise over a period of 8 h. The reaction mixture was then stirred for a further 24 h and freed of faults and unreacted reagents by ultrafiltration (30 kDa). Lyophilization resulted in a stable coupling product. About 55% of the insulin employed was recovered as HES conjugate.

EXAMPLE 16

Coupling of ox-HES-130 kDa to Superoxide Dismutase (SOD)

130 mg of ox-HES-130 kDa were completely dissolved in 6 ml of PBS pH 6, and then 10 mg of SOD (Roche, Mannheim) dissolved in 1 ml of PBS pH 6 were added. The coupling reaction was started by adding 10 mg of EDC. Addition of EDC was repeated every 3 h until 39 mg of the carbodiimide had been consumed. The reaction was monitored by GPC at 258 nm. After 24 h, 50% of the protein were found in the high molecular weight region of the separating column, and the reaction was stopped. The reaction mixture was dialyzed against 25 mM phosphate buffer pH 7.2 and lyophilized. The SOD activity was 95% of the initial activity. Determination of the mass distribution of HES protein samples by coupled GPC-light scattering revealed a molar ratio of HES to protein of 1:1.

EXAMPLE 17

Coupling of ox-HES 70 kDa to Glucagon

Glucagon ($66 \times 10^{-9}$ mol, 0.23 mg), oxHES 70 kDa ($6.6 \times 10^{-6}$ mol, 123 mg) were dissolved in phosphate buffer (1 ml, pH 5) in a round-bottom flask. 26 mg of EDC were added in 10 portions at intervals of 1 h. After a reaction time of 24 h, the reaction was stopped by adding 10 ml of water. The coupling product was purified by after dialysis against water by GPC and ion exchange chromatography. Freeze drying resulted in 88 mg of white coupling product (73%).

What is claimed is:

1. A hydroxyethyl starch-protein conjugate, characterized in that the binding interaction between the hydroxyethyl starch molecule and the protein is based on a covalent bond which is the result of a coupling reaction between (i) a functional group derived from the terminal aldehyde group of the hydroxyethyl starch molecule, which functional group is one of the functional groups of a bifunctional linker molecule with which the terminal aldehyde group has been reacted, and (ii) a functional group of the protein which is able to react with this functional group derived from the terminal aldehyde group of the hydroxyethyl starch molecule, where the bonding resulting directly in the coupling reaction can be modified by a further reaction to give the abovementioned covalent bonding.

2. The conjugate as claimed in claim 1, characterized in that the reactive functional group of the protein has been introduced into the protein by recombinant modification of the original amino acid sequence.

3. The conjugate as claimed in claim 1, wherein the functional group of the bifunctional linker molecule with which the terminal aldehyde group has been reacted is an amino group.

4. The conjugate as claimed in claim 1, wherein the functional group of the protein is an amino group, a thiol group, or an aldehyde or carboxyl group.

5. The conjugate as claimed in claim 4, wherein the functional group of the linker molecule which has been reacted with the functional group of the protein is an N-hydroxysuccinimide ester, a sulfo-N-hydroxysuccinimide ester, an imido ester, or another activated carboxyl group, a maleimide group or a carboxyl group, or an amino group or a thiol group.

6. The conjugate as claimed in claim 1, wherein between the two functional groups of the linker molecule, there is a biocompatible bridging molecule.

7. The conjugate as claimed in claim 6, wherein the biocompatible bridging molecule is a grouping derived from an alkane, an (oligo)alkylene glycol grouping, or another oligomer grouping.

8. The conjugate as claimed in claim 1, characterized in that the reactive functional group of the protein is one of the functional groups of a bifunctional linker molecule which has been coupled onto the protein.

9. The conjugate as claimed in claim 8, wherein the reactive functional group of the protein is an amino group, a thiol group, or an aldehyde or carboxyl group.

10. The conjugate as claimed in claim 9, wherein the group of the linker molecule able to enter into a covalent bonding with the functional group of the protein is an N-hydroxysuccinimide ester, a sulfo-N-hydroxysuccinimide ester, an imido ester, or another activated carboxyl group, a maleimide group or a carboxyl group, or an amino group or a thiol group.

11. The conjugate as claimed in claim 8, wherein between the two functional groups of the linker molecule which has been coupled onto the protein, there is a biocompatible bridging molecule.

12. The conjugate as claimed in claim 11, wherein the biocompatible bridging molecule is a grouping derived from an alkane, an (oligo)alkylene glycol grouping, or another oligomer grouping.

13. A pharmaceutical composition comprising an effective amount of a conjugate as claimed in claim 1 and a pharmaceutically acceptable carrier.

14. A method for preparing a hydroxyethyl starch-protein conjugate, characterized in that the binding interaction between the hydroxyethyl starch molecule and the protein is based on a covalent bond which is the result of a coupling reaction between (i) a functional group derived from the terminal aldehyde group of the hydroxyethyl starch molecule, which functional group is one of the functional groups of a bifunctional linker molecule with which the terminal aldehyde group has been reacted, and (ii) a functional group of the protein which is able to react with this functional group derived from the terminal aldehyde group of the hydroxyethyl starch molecule, where the bonding resulting directly in the coupling reaction can be modified by a further reaction to give the abovementioned covalent bonding, said method comprising:

(a) coupling in aqueous solution (i) a functional group derived from the terminal aldehyde group of the hydroxyethyl starch molecule by chemical reaction of the terminal aldehyde group with a bifunctional linker molecule, wherein said bifunctional linker molecule comprises at one end a group able to enter into a covalent bonding with the terminal aldehyde group, and at the other end a group able to enter into a covalent bonding with the functional group of the protein, and (ii) a functional group of the protein, which functional group is able to react with the functional group derived from the terminal aldehyde group of the hydroxyethyl starch molecule, and (b) modifying the bonding resulting directly from the coupling reaction by a further reaction.

15. The method as claimed in claim 14, characterized in that the reaction medium of the coupling reaction is water or a mixture of water and an organic solvent, where the water content of the mixture is at least 80%.

16. The method as claimed in claim 14, wherein the group of the linker molecule able to enter into a covalent bonding with the terminal aldehyde group is an amino group.

17. The method as claimed in claim 14, wherein the functional group of the protein is an amino group, a thiol group, or an aldehyde or carboxyl group.

18. The method as claimed in claim 17, wherein the group of the linker molecule able to enter into a covalent bonding with the functional group of the protein is an N-hydroxysuccinimide ester, a sulfo-N-hydroxysuccinimide ester, an imido ester, or another activated carboxyl group, a maleimide group or a carboxyl group, or an amino group or a thiol group.

19. The method as claimed in claim 14, wherein between the two functional groups of the linker molecule, there is a biocompatible bridging molecule.

20. The method as claimed in claim 19, wherein the biocompatible bridging molecule is a grouping derived from an alkane, an (oligo)alkylene glycol grouping, or another oligomer grouping.

21. The method as claimed in claim 14, wherein the functional group of the protein is one of the functional groups of a bifunctional linker molecule which has been coupled onto the protein, said linker molecule comprising at one end a grouping which is able to enter into a covalent bonding with a reactive functional group of the protein.

22. The method as claimed in claim 21, wherein the reactive functional group of the protein is an amino group, a thiol group, or an aldehyde or carboxyl group.

23. The method as claimed in claim 22, wherein the group of the linker molecule able to enter into a covalent bonding with the reactive functional group of the protein is an N-hydroxysuccinimide ester, a sulfo-N-hydroxysuccinimide ester, an imido ester, or another activated carboxyl group, a maleimide group or a carboxyl group, or an amino group or a thiol group.

24. The method as claimed in claim 21, wherein between the two functional groups of the linker molecule which has been coupled onto the protein, there is a biocompatible bridging molecule.

25. The method as claimed in claim 24, wherein the biocompatible bridging molecule is a grouping derived from an alkane, an (oligo)alkylene glycol grouping, or another oligomer grouping.

* * * * *